US010629300B2

(12) United States Patent
Dintenfass et al.

(10) Patent No.: US 10,629,300 B2
(45) Date of Patent: Apr. 21, 2020

(54) GEOGRAPHIC SELECTION SYSTEM BASED ON RESOURCE ALLOCATION AND DISTRIBUTION

(71) Applicant: BANK OF AMERICA CORPORATION, Charlotte, NC (US)

(72) Inventors: Katherine Dintenfass, Lincoln, RI (US); Vasudevan Nagalingam, Wayland, MA (US)

(73) Assignee: BANK OF AMERICA CORPORATION, Charlotte, NC (US)

( * ) Notice: Subject to any disclaimer, the term of this patent is extended or adjusted under 35 U.S.C. 154(b) by 133 days.

(21) Appl. No.: 15/223,458

(22) Filed: Jul. 29, 2016

(65) Prior Publication Data
US 2017/0323384 A1    Nov. 9, 2017

Related U.S. Application Data

(60) Provisional application No. 62/333,723, filed on May 9, 2016.

(51) Int. Cl.
*G06Q 40/00* (2012.01)
*G16H 40/63* (2018.01)
(Continued)

(52) U.S. Cl.
CPC ........... *G16H 40/63* (2018.01); *G06F 16/176* (2019.01); *G06F 16/248* (2019.01); *G06F 16/29* (2019.01);
(Continued)

(58) Field of Classification Search
CPC ..................................................... G06Q 40/08
(Continued)

(56) References Cited

U.S. PATENT DOCUMENTS 5,586,240 A    12/1996 Khan et al.
5,920,848 A    7/1999 Schutzer et al.
(Continued)

FOREIGN PATENT DOCUMENTS

WO    0118728 A2    3/2001
WO    2003100645 A1    12/2003
(Continued)

OTHER PUBLICATIONS

Money Management Online Money Management Software mint. com (Year: 2009).*

(Continued)

*Primary Examiner* — Bruce I Ebersman
(74) *Attorney, Agent, or Firm* — Michael A. Springs; Moore & Van Allen PLLC; Nicholas C. Russell

(57) ABSTRACT

Embodiments of the invention are directed to a system, method, or computer program product for triggering of living option resource allocation. In some embodiments, the invention provides a system for triggering of a model generation for location selection. As such, the system may interconnect with market analysis devices, medical devices, and home repair associates to determine resource availability and requirement for location selection. In this way, the system generates a real-time interactive indication of location selection for the user. Furthermore, a decision tool may be linked to a trusted individual associated with the user and provided upon generation to the individual.

14 Claims, 10 Drawing Sheets

(51) Int. Cl.

| | | |
|---|---|---|
| *G06Q 40/06* | (2012.01) | |
| *G06F 16/29* | (2019.01) | |
| *G06F 16/176* | (2019.01) | |
| *G06F 16/248* | (2019.01) | |
| *G06F 16/335* | (2019.01) | |
| *G06F 16/9535* | (2019.01) | |
| *G06F 16/9537* | (2019.01) | |
| *H04L 29/08* | (2006.01) | |
| *H04L 29/06* | (2006.01) | |
| *G06Q 30/02* | (2012.01) | |
| *G06Q 30/06* | (2012.01) | |
| *G06Q 20/38* | (2012.01) | |
| *G06Q 20/40* | (2012.01) | |
| *G06Q 50/00* | (2012.01) | |
| *G06F 21/62* | (2013.01) | |
| *G06Q 10/10* | (2012.01) | |
| *G06F 19/00* | (2018.01) | |
| *G06Q 50/16* | (2012.01) | |

(52) U.S. Cl.
CPC ........ *G06F 16/335* (2019.01); *G06F 16/9535* (2019.01); *G06F 16/9537* (2019.01); *G06F 19/00* (2013.01); *G06F 21/6245* (2013.01); *G06Q 10/1057* (2013.01); *G06Q 20/3821* (2013.01); *G06Q 20/4014* (2013.01); *G06Q 30/0201* (2013.01); *G06Q 30/0226* (2013.01); *G06Q 30/0645* (2013.01); *G06Q 40/06* (2013.01); *G06Q 50/01* (2013.01); *H04L 63/08* (2013.01); *H04L 63/083* (2013.01); *H04L 67/10* (2013.01); *H04L 67/18* (2013.01); *H04L 67/20* (2013.01); *H04L 67/306* (2013.01); *G06Q 50/16* (2013.01)

(58) Field of Classification Search
USPC .......................................................... 705/4
See application file for complete search history.

(56) References Cited

U.S. PATENT DOCUMENTS

| | | |
|---|---|---|
| 5,987,433 A | 11/1999 | Crapo |
| 6,014,632 A * | 1/2000 | Gamble ................ G06F 19/328 705/2 |
| 6,208,992 B1 | 3/2001 | Bruckner |
| 6,684,190 B1 | 1/2004 | Powers et al. |
| 6,985,880 B1 | 1/2006 | Hodgdon et al. |
| 7,062,572 B1 | 6/2006 | Hampton |
| 7,069,308 B2 | 6/2006 | Abrams |
| 7,174,313 B1 | 2/2007 | Martinez |
| 7,216,099 B2 | 5/2007 | Chen et al. |
| 7,295,832 B2 | 11/2007 | Hewel |
| 7,295,999 B1 | 11/2007 | Simon et al. |
| 7,299,007 B2 | 11/2007 | Eskin |
| 7,475,032 B1 | 1/2009 | Patnode et al. |
| 7,634,436 B1 | 12/2009 | Wagner |
| 7,657,655 B2 | 2/2010 | Hampton |
| 7,660,744 B2 | 2/2010 | Philippe et al. |
| 7,668,764 B2 | 2/2010 | Wilson |
| 7,725,387 B1 | 5/2010 | Fitch et al. |
| 7,822,671 B1 | 10/2010 | Oros |
| 7,840,463 B1 | 11/2010 | Davis |
| 7,840,470 B2 | 11/2010 | Robinson |
| 7,865,419 B2 | 1/2011 | Rojeck et al. |
| 7,895,102 B1 | 2/2011 | Wilks et al. |
| 7,945,458 B1 * | 5/2011 | Jackson ................ G06Q 10/10 705/2 |
| 7,949,592 B1 | 5/2011 | Oros |
| 8,050,995 B1 | 11/2011 | Landry et al. |
| 8,069,103 B1 | 11/2011 | Davis |
| 8,332,297 B1 | 12/2012 | Claus et al. |
| 8,429,091 B2 | 4/2013 | Buyukkokten et al. |
| 8,458,044 B2 | 6/2013 | Blair et al. |
| 8,484,109 B1 | 7/2013 | Nelson Deurmier et al. |
| 8,504,435 B2 | 8/2013 | Charles |
| 8,527,382 B2 | 9/2013 | McDonough et al. |
| 8,551,186 B1 | 10/2013 | Strand |
| 8,567,672 B2 | 10/2013 | Mesaros |
| 8,590,785 B1 | 11/2013 | Mesaros |
| 8,606,630 B2 | 12/2013 | Fordyce, III et al. |
| 8,635,226 B2 | 1/2014 | Chang et al. |
| 8,639,567 B2 | 1/2014 | Winters |
| 8,639,622 B1 | 1/2014 | Moore et al. |
| 8,639,650 B1 | 1/2014 | Gill |
| 8,676,687 B2 | 3/2014 | McDonough et al. |
| 8,688,556 B2 | 4/2014 | Greene et al. |
| 8,719,132 B1 | 5/2014 | Diggdon et al. |
| 8,782,136 B1 | 7/2014 | Ho et al. |
| 9,002,272 B2 | 4/2015 | Friedlaender |
| 9,064,284 B1 | 6/2015 | Janiszeski et al. |
| 9,077,677 B2 | 7/2015 | Mackin |
| 9,501,624 B2 * | 11/2016 | Vishnubhatla ........ G06F 19/328 |
| 10,096,033 B2 * | 10/2018 | Heath .................... G06Q 30/02 |
| 10,227,063 B2 * | 3/2019 | Abreu ................ B60H 1/00742 |
| 10,340,034 B2 * | 7/2019 | Hyde ..................... G16H 40/67 |
| 10,365,811 B2 | 7/2019 | Robinson et al. |
| 10,475,142 B2 * | 11/2019 | Hyde ..................... G16H 10/60 |
| 2002/0107849 A1 | 8/2002 | Hickey et al. |
| 2002/0133706 A1 | 9/2002 | Khanna et al. |
| 2002/0198801 A1 | 12/2002 | Dixon et al. |
| 2003/0028466 A1 * | 2/2003 | Jenson ................... G06Q 40/00 705/36 R |
| 2003/0105692 A1 | 6/2003 | Gilbert et al. |
| 2003/0233278 A1 | 12/2003 | Marshall |
| 2004/0111370 A1 | 6/2004 | Saylors et al. |
| 2004/0177036 A1 | 9/2004 | Nutahara et al. |
| 2004/0243631 A1 | 12/2004 | Walker et al. |
| 2004/0255218 A1 | 12/2004 | Tada et al. |
| 2005/0080725 A1 | 4/2005 | Pick |
| 2005/0096973 A1 | 5/2005 | Heyse et al. |
| 2005/0144108 A1 | 6/2005 | Loeper |
| 2005/0149436 A1 | 7/2005 | Elterich |
| 2005/0195221 A1 | 9/2005 | Berger et al. |
| 2005/0198305 A1 | 9/2005 | Pezaris et al. |
| 2006/0026018 A1 | 2/2006 | Exner et al. |
| 2006/0031150 A1 | 2/2006 | Senturk et al. |
| 2006/0224435 A1 | 10/2006 | Male et al. |
| 2007/0099166 A1 | 5/2007 | Moesges et al. |
| 2007/0192224 A1 | 8/2007 | Quayle et al. |
| 2007/0250427 A1 | 10/2007 | Robinson |
| 2007/0282699 A1 | 12/2007 | Kumar et al. |
| 2007/0288399 A1 | 12/2007 | Reynolds et al. |
| 2008/0040276 A1 | 2/2008 | Hammad et al. |
| 2008/0109412 A1 | 5/2008 | Drayer et al. |
| 2008/0189189 A1 | 8/2008 | Morgenstern |
| 2008/0215501 A1 | 9/2008 | Rojeck et al. |
| 2008/0217397 A1 | 9/2008 | Degliantoni et al. |
| 2008/0270304 A1 | 10/2008 | Brown |
| 2008/0300893 A1 | 12/2008 | Mendoza et al. |
| 2009/0024540 A1 | 1/2009 | Ryder |
| 2009/0030819 A1 | 1/2009 | VanLeeuwen |
| 2009/0089448 A1 | 4/2009 | Sze et al. |
| 2009/0146947 A1 | 6/2009 | Ng |
| 2009/0204528 A1 | 8/2009 | Moses |
| 2009/0307314 A1 | 12/2009 | Smith et al. |
| 2009/0326339 A1 | 12/2009 | Horvitz |
| 2009/0327308 A1 | 12/2009 | Carter et al. |
| 2010/0030686 A1 | 2/2010 | Lee et al. |
| 2010/0057574 A1 | 3/2010 | Banerjee et al. |
| 2010/0094740 A1 | 4/2010 | Richter |
| 2010/0100469 A1 | 4/2010 | Buchanan et al. |
| 2010/0205112 A1 | 8/2010 | Reynolds et al. |
| 2010/0211411 A1 | 8/2010 | Hudson |
| 2010/0241559 A1 | 9/2010 | O'Connor et al. |
| 2010/0268629 A1 | 10/2010 | Ross et al. |
| 2010/0274610 A1 | 10/2010 | Andersen et al. |
| 2010/0306126 A1 | 12/2010 | Moran et al. |
| 2010/0318372 A1 | 12/2010 | Band et al. |
| 2011/0055008 A1 | 3/2011 | Feuerstein et al. |
| 2011/0106631 A1 | 5/2011 | Lieberman et al. |
| 2011/0106682 A1 | 5/2011 | Rojeck et al. |

(56) References Cited

U.S. PATENT DOCUMENTS

| | | |
|---|---|---|
| 2011/0106691 A1 | 5/2011 | Clark et al. |
| 2011/0131089 A1 | 6/2011 | Walker et al. |
| 2011/0166978 A1 | 7/2011 | Mastrogiovanni |
| 2011/0191173 A1 | 8/2011 | Blackhurst et al. |
| 2011/0213665 A1 | 9/2011 | Joa et al. |
| 2011/0231305 A1 | 9/2011 | Winters |
| 2011/0246279 A1 | 10/2011 | Joa et al. |
| 2011/0246306 A1 | 10/2011 | Blackhurst et al. |
| 2011/0276410 A1 | 11/2011 | Hjelm et al. |
| 2012/0047022 A1 | 2/2012 | Shamim et al. |
| 2012/0123857 A1 | 5/2012 | Surve et al. |
| 2012/0214571 A1 | 8/2012 | Oakes et al. |
| 2012/0265819 A1 | 10/2012 | McGann et al. |
| 2012/0284127 A1 | 11/2012 | Heiser, II et al. |
| 2013/0006756 A1 | 1/2013 | Heo |
| 2013/0018813 A1 | 1/2013 | Carroll et al. |
| 2013/0046645 A1 | 2/2013 | Grigg et al. |
| 2013/0073388 A1 | 3/2013 | Heath |
| 2013/0073546 A1 | 3/2013 | Yan et al. |
| 2013/0096996 A1 | 4/2013 | Tabor et al. |
| 2013/0150139 A1 | 6/2013 | Oakes |
| 2013/0179254 A1 | 7/2013 | Joa et al. |
| 2013/0246147 A1 | 9/2013 | Chen et al. |
| 2013/0282594 A1 | 10/2013 | Gaedcke et al. |
| 2013/0325748 A1* | 12/2013 | Suri ................ G06Q 40/06 705/36 R |
| 2014/0032293 A1 | 1/2014 | Donlan et al. |
| 2014/0046748 A1 | 2/2014 | Nagarajan et al. |
| 2014/0114674 A1* | 4/2014 | Krughoff .......... G06Q 30/0629 705/2 |
| 2014/0114882 A1 | 4/2014 | Thoma |
| 2014/0136323 A1 | 5/2014 | Zhang et al. |
| 2014/0149303 A1 | 5/2014 | Band et al. |
| 2014/0188656 A1 | 7/2014 | Puttaswamy et al. |
| 2014/0230019 A1 | 8/2014 | Civelli et al. |
| 2014/0280757 A1 | 9/2014 | Tran |
| 2014/0282877 A1 | 9/2014 | Mahaffey et al. |
| 2014/0324559 A1 | 10/2014 | Sheehy et al. |
| 2014/0380445 A1 | 12/2014 | Tunnell et al. |
| 2015/0019523 A1 | 1/2015 | Lior et al. |
| 2015/0040203 A1 | 2/2015 | Qian |
| 2015/0119070 A1 | 4/2015 | Harris et al. |
| 2015/0134353 A1* | 5/2015 | Ferrell ............ G06Q 30/0623 705/2 |
| 2015/0178844 A1 | 6/2015 | Ross et al. |
| 2015/0228000 A1 | 8/2015 | Bijor et al. |
| 2015/0363562 A1 | 12/2015 | Hallwachs |
| 2015/0363563 A1 | 12/2015 | Hallwachs |
| 2016/0012249 A1 | 1/2016 | Keppler |
| 2016/0027079 A1 | 1/2016 | Schoeffler |
| 2016/0063410 A1 | 3/2016 | Tsay et al. |
| 2016/0086294 A1 | 3/2016 | Khamis |
| 2016/0171410 A1 | 6/2016 | Sun et al. |
| 2016/0171574 A1 | 6/2016 | Paulucci et al. |
| 2016/0239931 A1 | 8/2016 | Sabri et al. |
| 2016/0275615 A1 | 9/2016 | Dintenfass et al. |
| 2016/0324442 A1 | 11/2016 | Zdeblick |
| 2017/0019496 A1* | 1/2017 | Orbach ................ H04L 67/306 |
| 2017/0046758 A1 | 2/2017 | Sheehan et al. |
| 2017/0193404 A1 | 7/2017 | Yoo et al. |
| 2017/0293878 A1 | 10/2017 | Donnelly et al. |
| 2018/0096425 A1 | 4/2018 | Simon et al. |

FOREIGN PATENT DOCUMENTS

| | | |
|---|---|---|
| WO | 2005059799 A2 | 6/2005 |
| WO | 2010045058 A1 | 4/2010 |
| WO | 2010045059 A1 | 4/2010 |
| WO | 2013008128 A1 | 1/2013 |
| WO | 2014104436 A1 | 7/2014 |
| WO | 2015034937 A1 | 3/2015 |
| WO | 2015192121 A1 | 12/2015 |

OTHER PUBLICATIONS http://budgettracker.com retrieved on Jun. 9, 2009.
http://buxfer.com retrieved on Jun. 9, 2009.
http://personal.fidelity.com/planning/retirement/retiree/content/imademo.shtml# retrieved on Sep. 24, 2008.
http://www.mint.com/features/auto/ retrieved on Jul. 99, 2009.
http://www.mvelopes.com/overview retrieved on Jun. 9, 2009.
http://www.nytimes.com/2008/12/07/weekinreview/07dash.html?_r=3&ref=weekinreview retrieved on Mar. 27, 2009.
http://www.pncvirtualwallet.com/main.html retrieved on Nov. 24, 2008.
http://yodlee.com/solutions_pfm_ypf.shtml retrieved on Jun. 9, 2009.
http:/www.digitalreceipts.com retrieved on Jun. 11, 2009.
https://www.budgetpulse.com retrieved on Jun. 9, 2009.
https://www.pearbudget.com retrieved on Jun. 9, 2009.
International Search Report for International Application PCT/US2010/35192 dated Jul. 8, 2010.
International Search Report for International Application PCT/US2010/30672 dated Jun. 7, 2010.
International Search Report for International Application PCT/US2010/02162 dated May 2, 2011.

* cited by examiner

GEOGRAPHIC SELECTION SYSTEM BASED ON RESOURCE ALLOCATION AND DISTRIBUTION

CROSS-REFERENCE TO RELATED APPLICATIONS

This application is a continuation of U.S. Provisional Patent Application Ser. No. 62/333,723, filed May 9, 2016, entitled "System for Optimizing Resource Usage," the entirety of which is incorporated herein by reference.

BACKGROUND

With advancements in machine and product development, systems and applications for social connection and location identifications are being developed. These interconnections allow for system development and resource deployment avenues. However, there is a need for a unified system for system development for connection to efficiently and conveniently fulfill various requests through sharing of resources deployment.

BRIEF SUMMARY

Usage of finite resources in a period of possible resource depletion can be difficult to navigate. Inefficient usage of resources can cause early depletion. Different geographic areas may provide differentiation in resource requirements, which can effect resource usage. By surveying the differences in geographic locations and determining optimized efficient resource usage, a system can provide an optimization resource usage plan.

Embodiments of the present invention address the above needs and/or achieve other advantages by providing apparatuses (e.g., a system, computer program product, and/or other device) and methods that improve resource usage planning, such as retirement planning, for users (e.g., customers) and allows the users to factor in different variables (e.g., age, spending amounts over time, events that may affect retirement planning, or the like).

In some embodiments, the invention generates and maintains of a modeling tool for pre-retirees for determination of location of living when aging. The modeling tool may take into consideration costs for assisted living, medical expenses, user's budget and expenses, remodeling of current home requirements, and the like. The model may determine or provide options and prices for aging in place or in a care facility. The model would compare costs to living in home, including modifications to the home required for living in place, home health care, and the like compared to costs of care facilities in the area. The model is generated based on finances and health, such as illnesses, or the like that may impact the living selection. Decision tool may be provided to trusted family members, doctors for input on determination, and insurance providers. Furthermore, the model may be integrated with a mechanism for the sharing of information to trusted individuals throughout the process of modeling such that the decision processing may be taking place during the process and not specifically presenting the final modeling to the user and trusted individual at the final stage.

Embodiments of the invention relate to systems, methods, and computer program products for accessing and analyzing resources for retirement planning, the invention comprising: accessing the resources of a user over a network of servers, wherein the resources include illiquid resources and liquid resources; determining asset values; determining user information, wherein user information comprises medical and age information for the user; determining resource in-flows and resource out-flows for the resources over a past time period by analyzing transactions for the resources; calculating estimated future resource in-flows and estimated future resource out-flows over a future time period from at least the resource in-flows and the resource out-flows; determining estimated rates of return for the resources that provide returns; receiving selected location preferences from them user; generating a model of the selected location preferences of the user and alternative locations identified for the user; calculating location selection options for the user within the user's estimate future resource in-flows and estimated future resource out-flows, based on the selected location preferences and the alternative locations identified compared to the estimated future resource in-flows and estimated future resource out-flows over the future time period from at least the resource in-flows and the resource out-flows; and displaying the location selection options to the user using the model via a display on a device associated with the user.

In some embodiments, the invention further comprises generating, upon display of the location selection options to the user, a decision tool that is queued and sent to one or more trusted individual associated with the user illustrating the location selection options and the user selected location selection options for implementation, wherein the trusted individual is a family member or resource allocation planner.

In some embodiments, displaying the location selection options to the user using the model via a display on a device associated with the user further comprises an interactive map overlay of the location selection options for user selection.

In some embodiments, receiving location selection preferences from a user further comprises providing the user with an interactive display that includes location selection preferences such as staying in a current location, remodeling the current location, moving to an alternative location, or moving to a care facility.

In some embodiments, calculating location selection options further comprises identifying a resource amount required for the location for one or more time periods and an age parameter, wherein the available resource amount indicates estimated resources the user is safe to spend on the location based on the user's estimate future resource in-flows and estimated future resource out-flows, wherein the age parameter indicates an estimated age when asset values will be depleted, and wherein the available resource amount for the time period and the age parameter are based at least in part on the asset values, the estimated rates of return, the estimated future resource in-flows and the estimated future resource out-flows.

In some embodiments, the invention further comprises maintaining the model of the location preferences and alternative locations in real-time, such that the model considers real-time resource requirements for assisted living, medical expenses, remodeling of current location, and user in-flows and out-flows.

In some embodiments, the location preferences or alternative locations comprise a current home, modification of the current home, care facilities, home health care, or alternative living arrangements.

The features, functions, and advantages that have been discussed may be achieved independently in various embodiments of the present invention or may be combined with yet other embodiments, further details of which can be seen with reference to the following description and drawings.

BRIEF DESCRIPTION OF THE DRAWINGS

Figure 1:
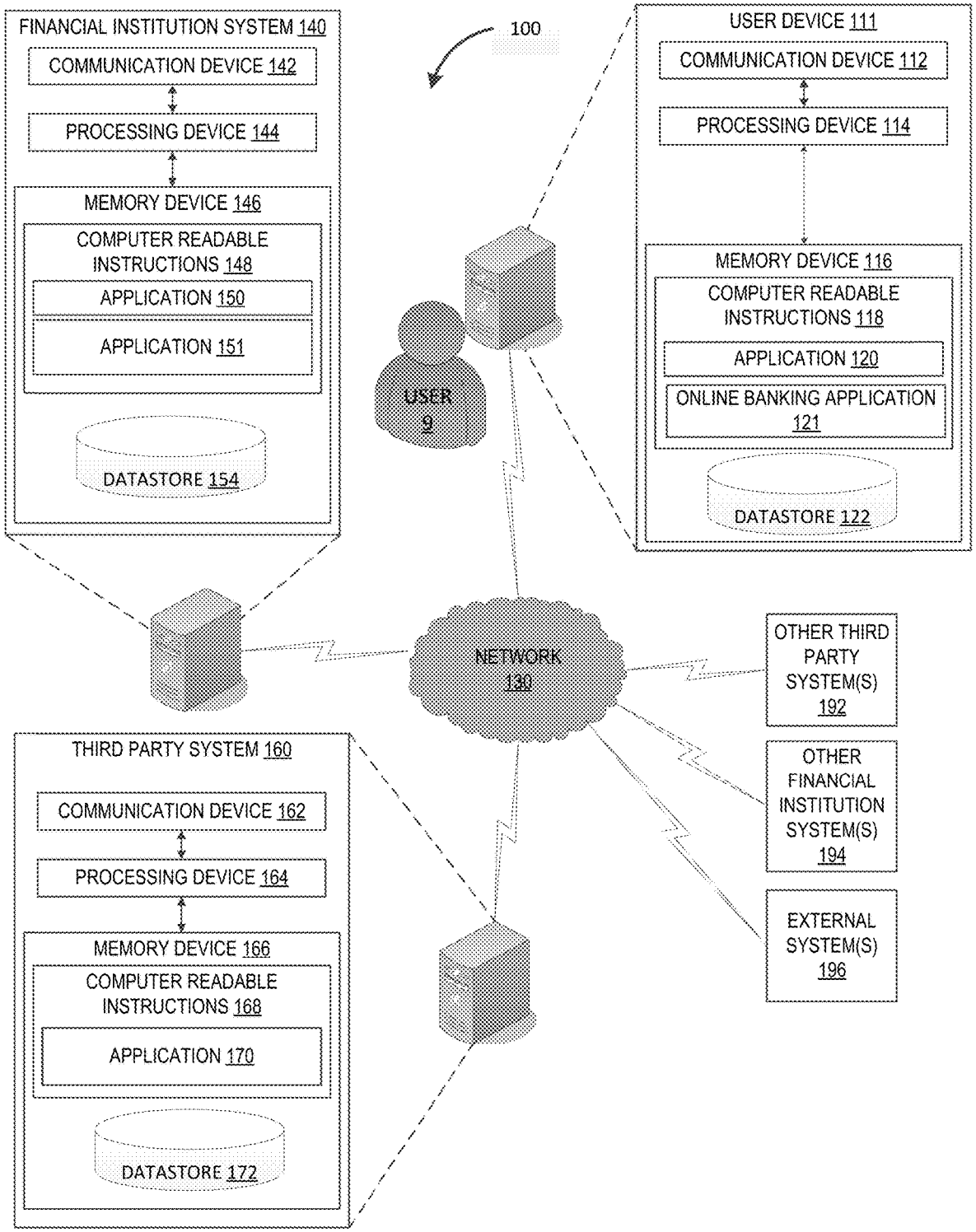
Figure 2:
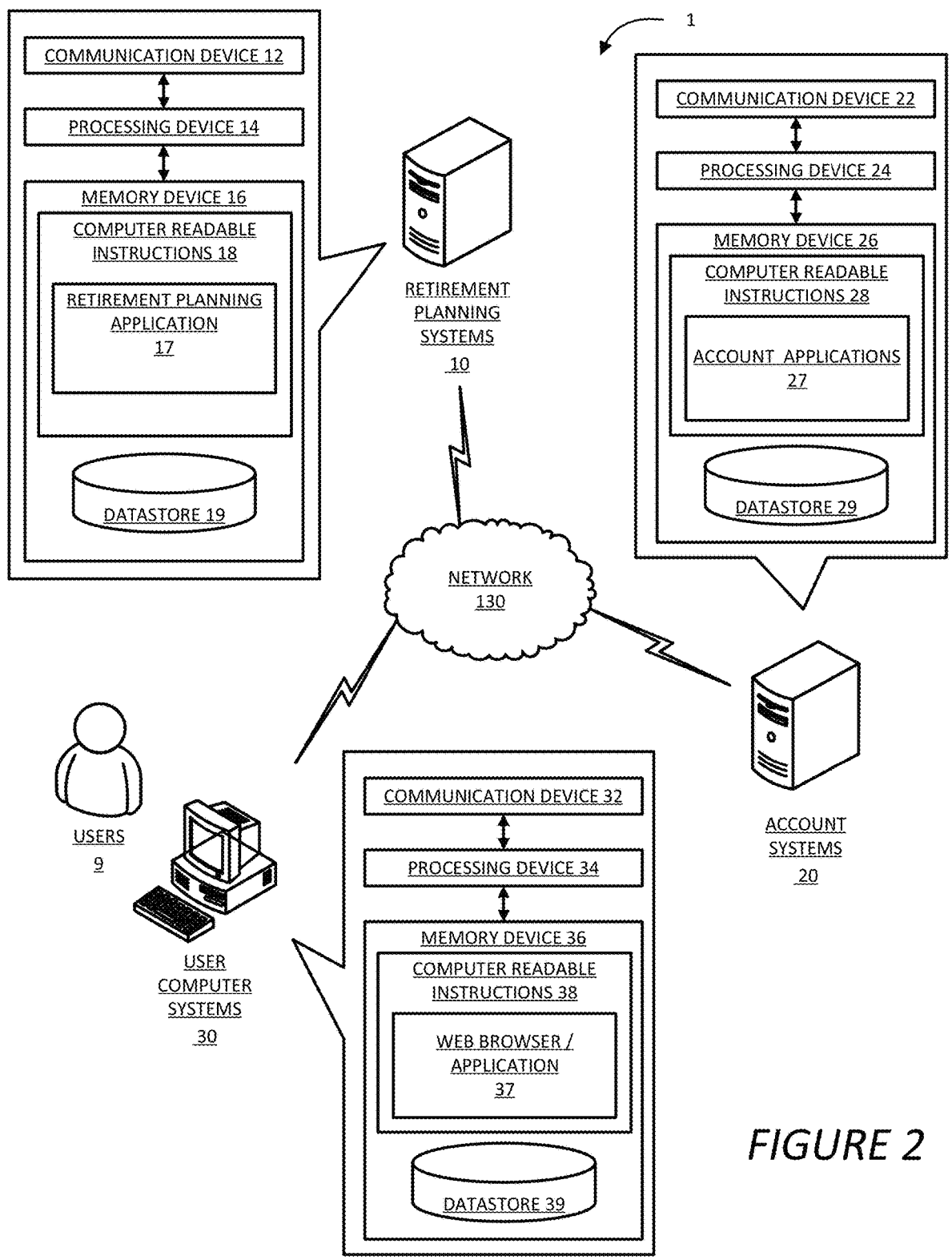
Figure 3:
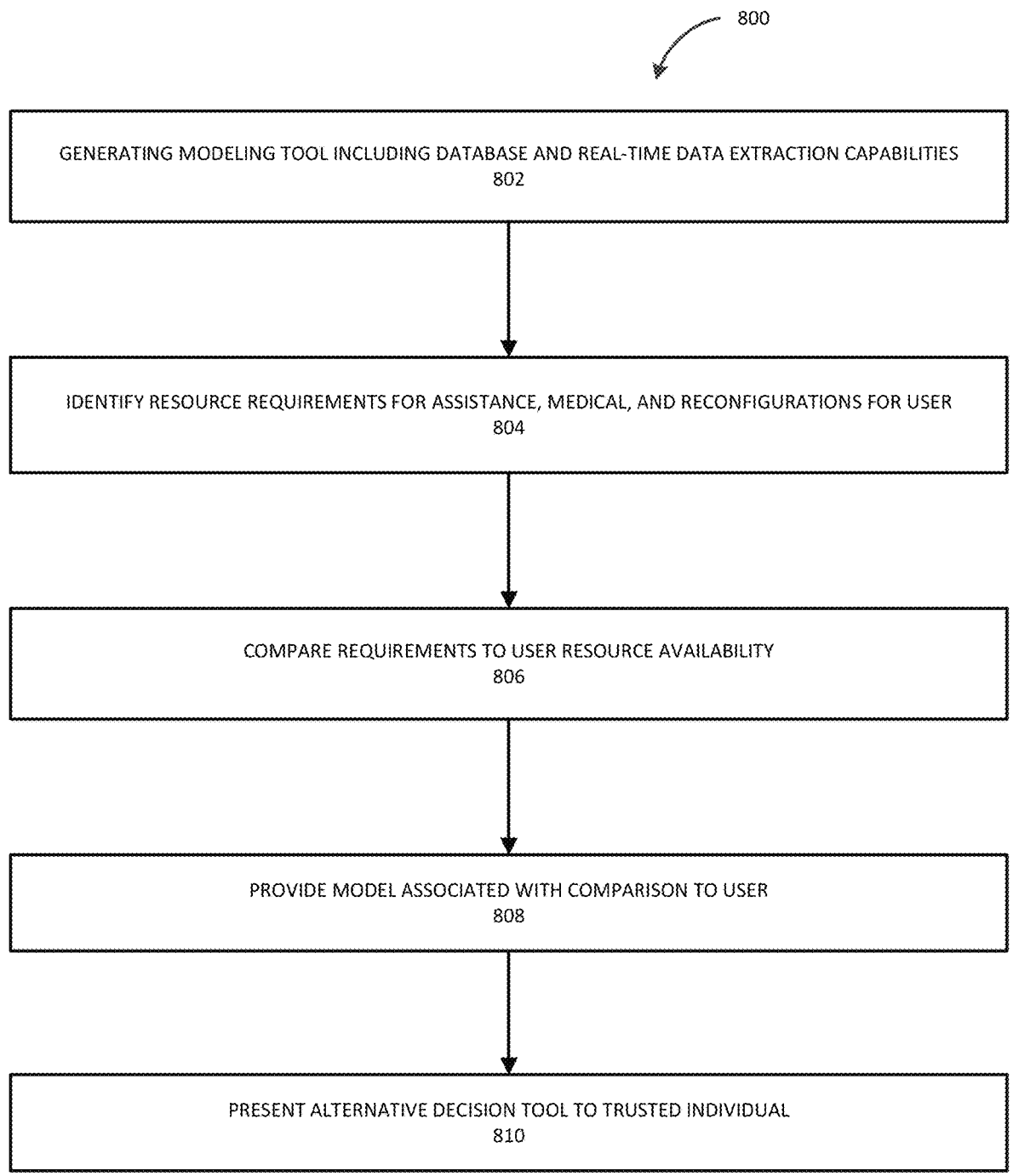
Figure 4:
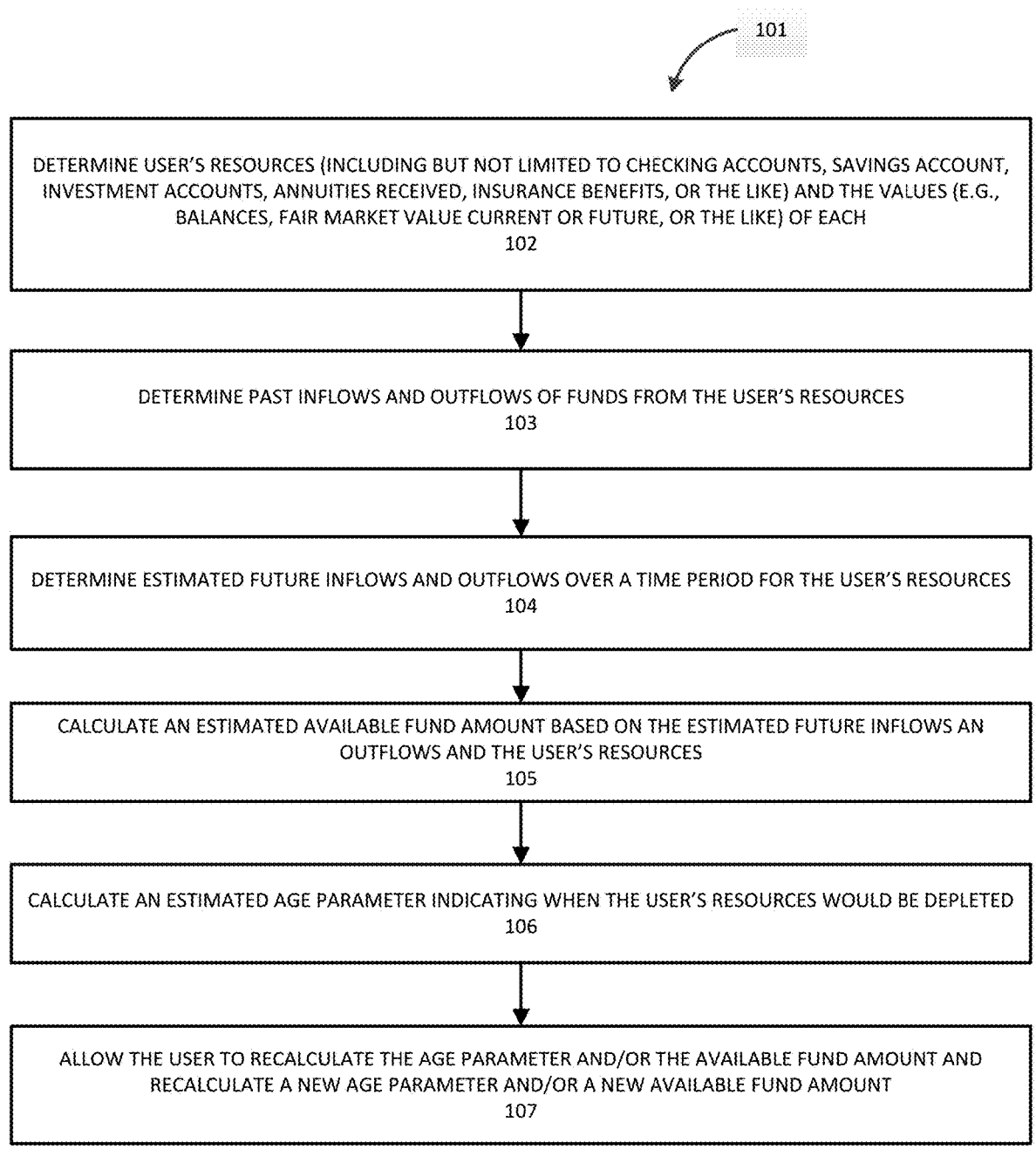
Figure 5:
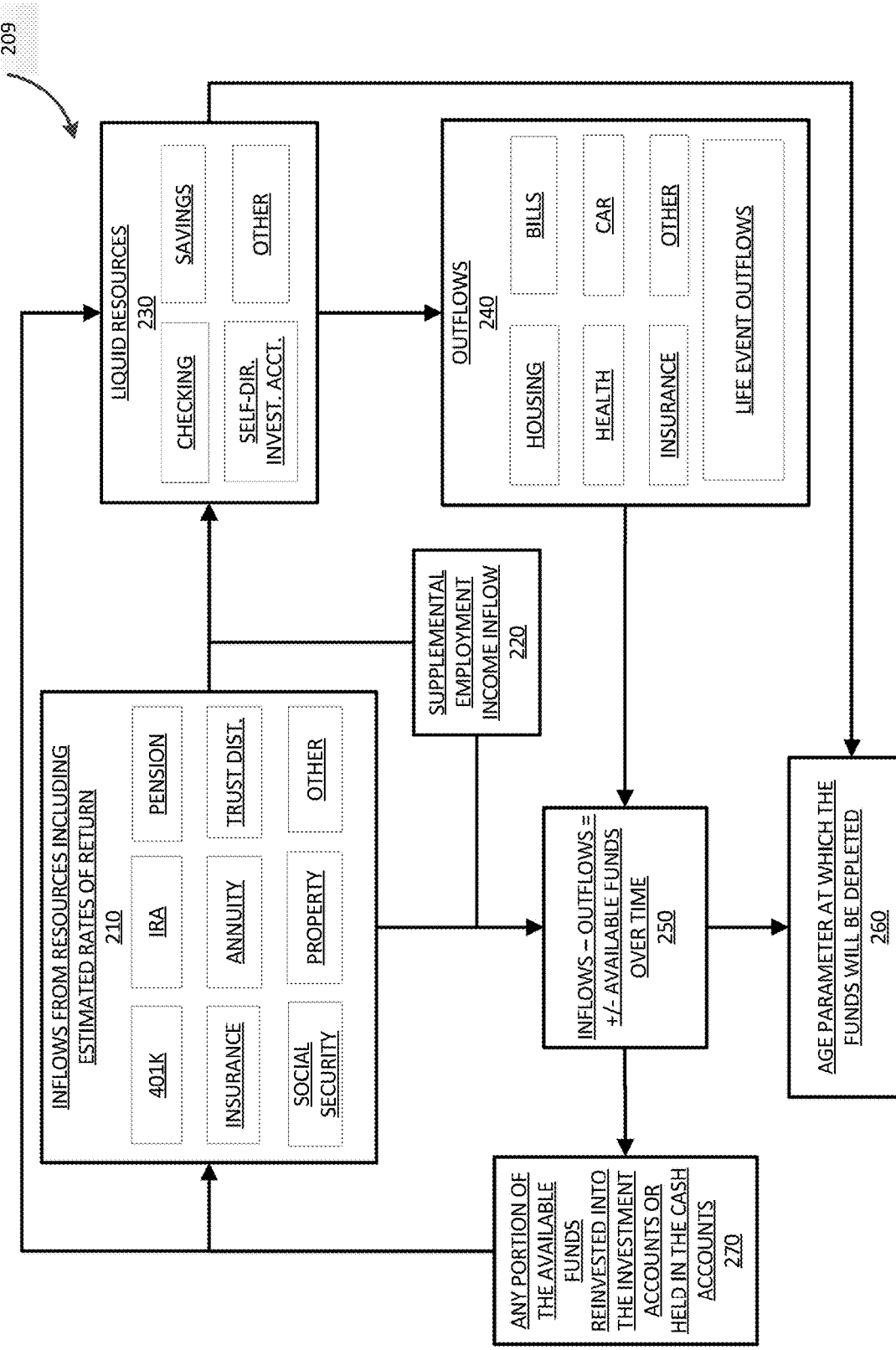
Figure 6:
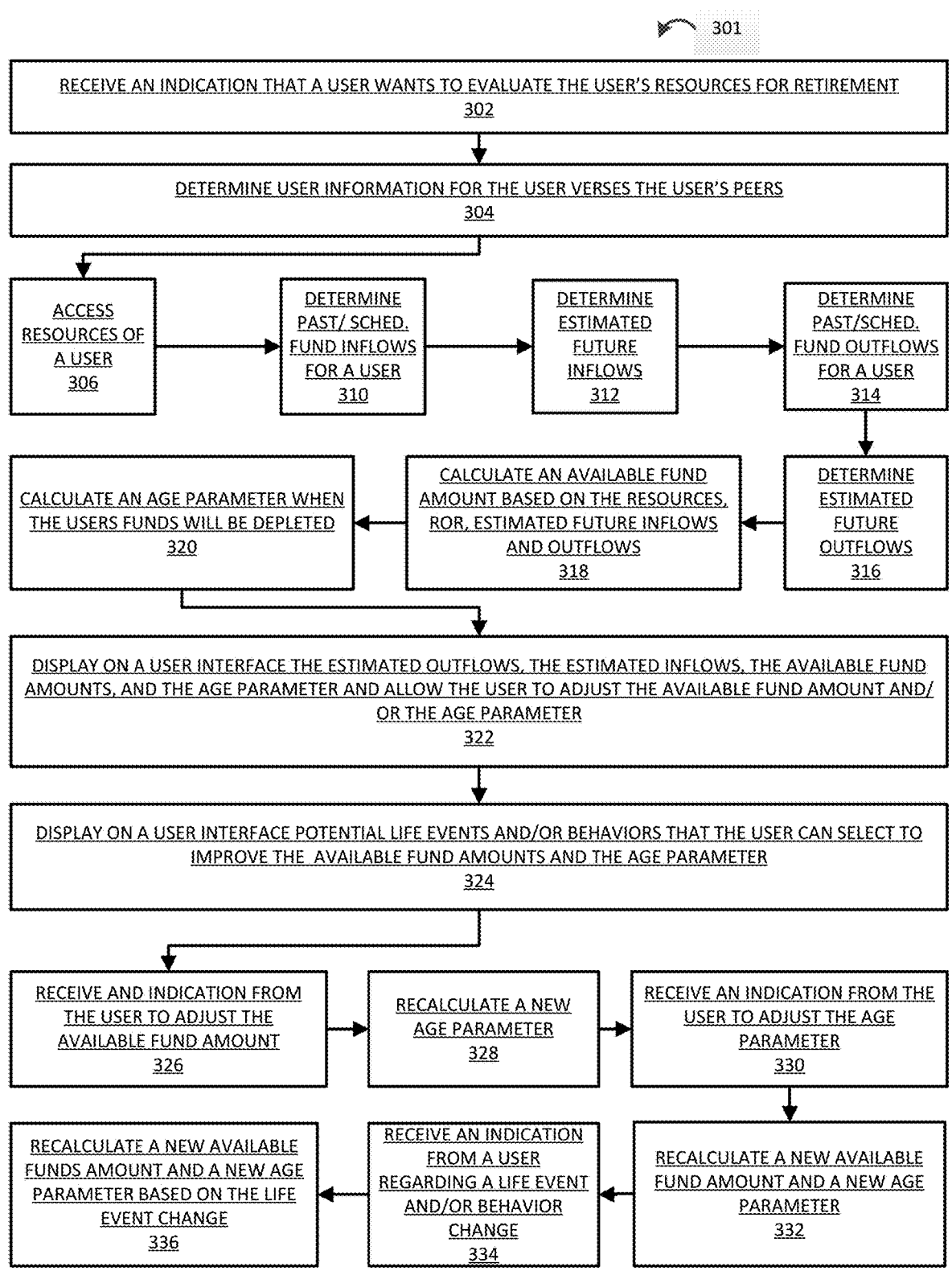
Figure 7:
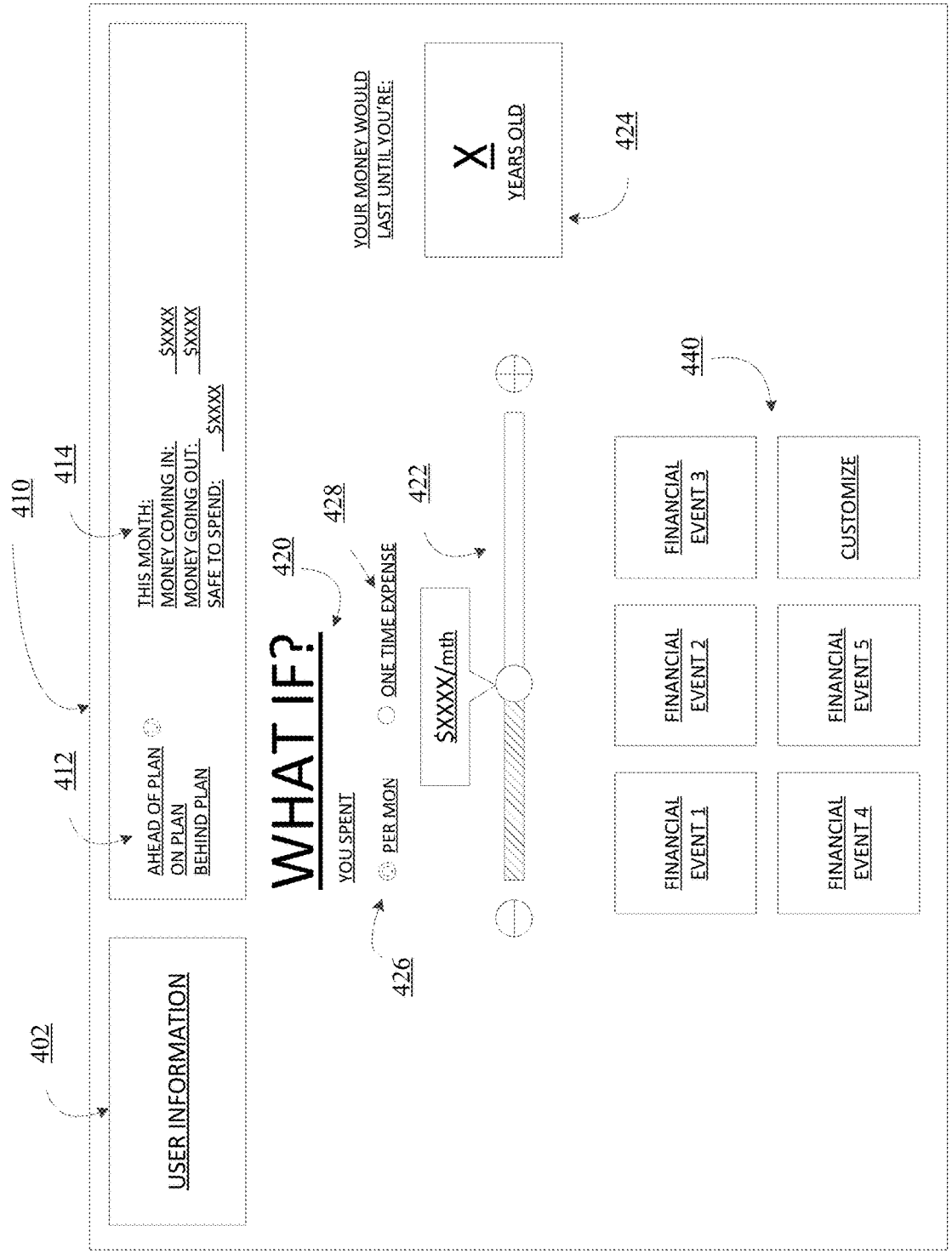
Figure 8:
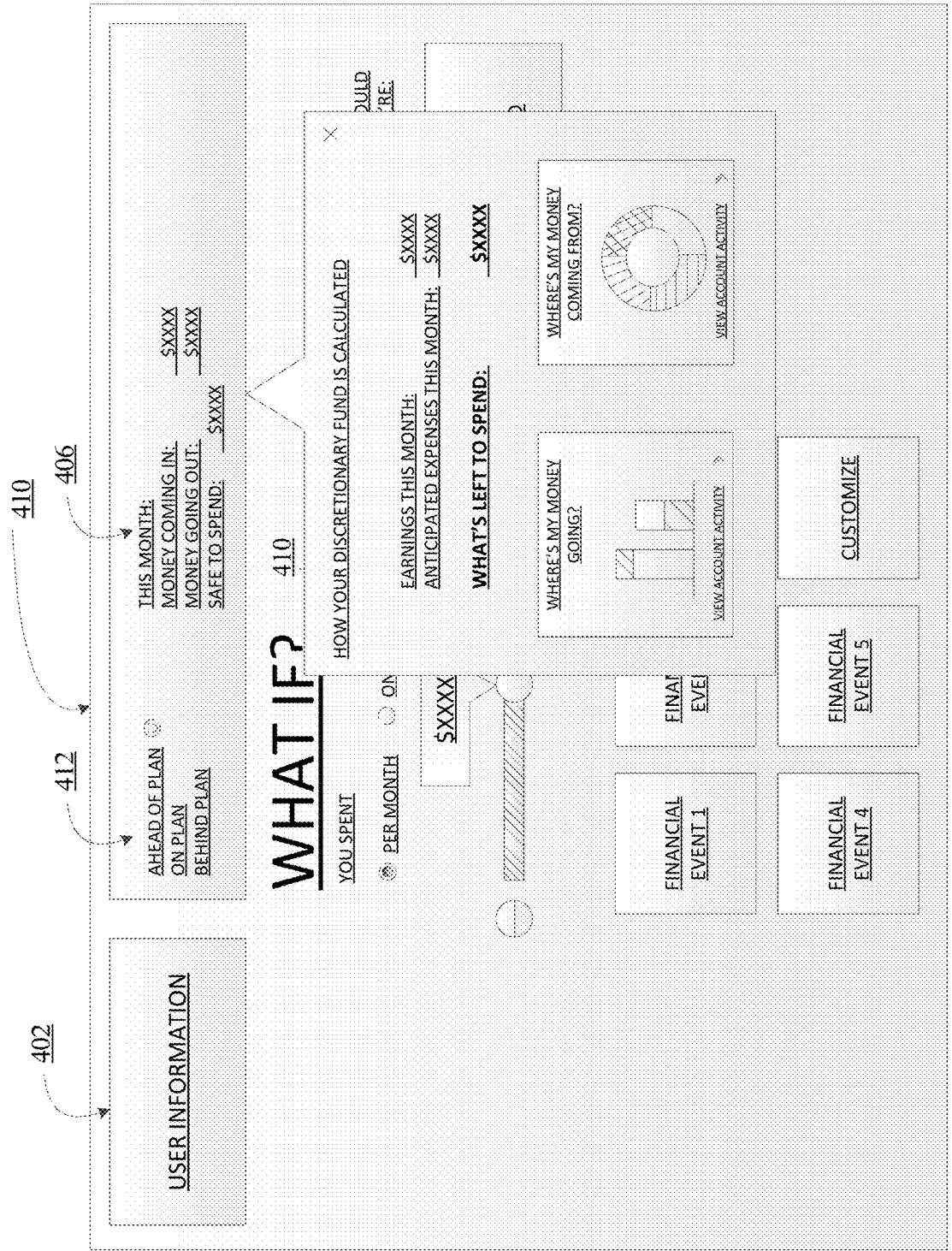
Figure 9:
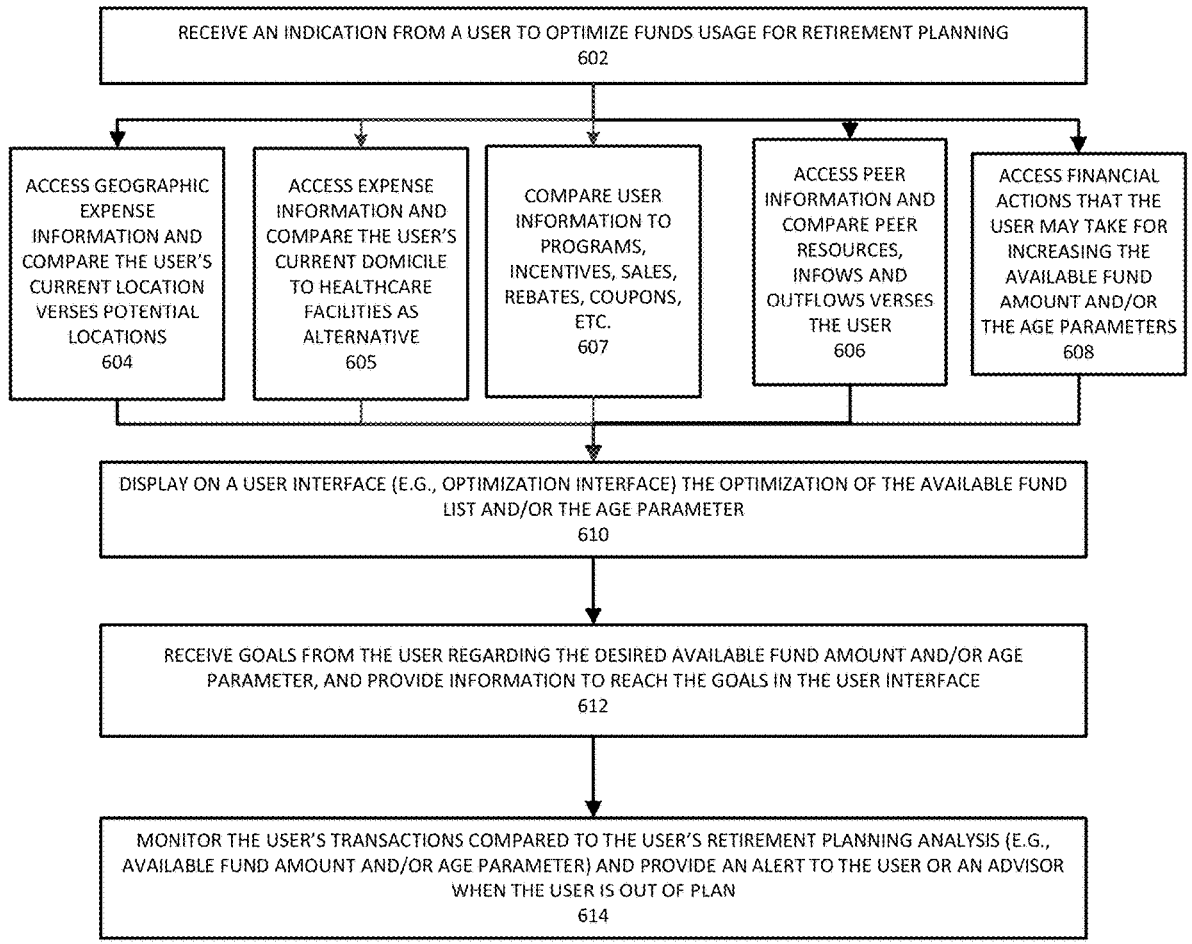
Figure 10:
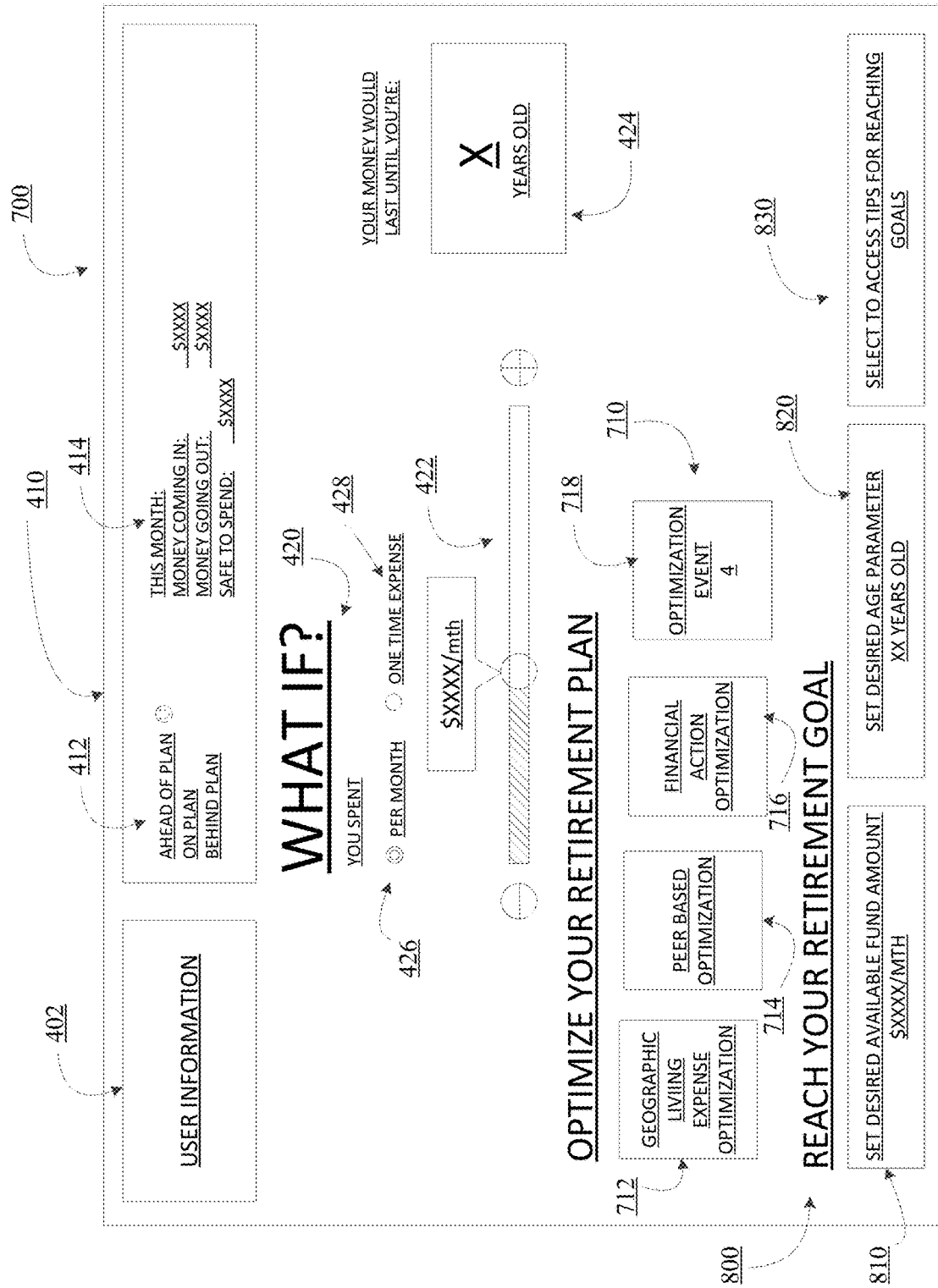

Having thus described embodiments of the invention in general terms, reference will now be made to the accompanying drawings, wherein:

FIG. 1 illustrates a geographic selection system environment, in accordance with one embodiment of the present invention;

FIG. 2 illustrates a block system diagram for a retirement planning system environment, in accordance with one embodiment of the present invention;

FIG. 3 illustrates a high level process flow for graphic selection based on resource allocation and distribution, in accordance with one embodiment of the present invention;

FIG. 4 illustrates a high level process flow for retirement planning based on resource distributions, in accordance with one embodiment of the present invention;

FIG. 5 illustrates a flow indicating how the available resource amount and/or an age parameter are influenced, in accordance with one embodiment of the invention;

FIG. 6 illustrates a detailed process flow for retirement planning based on resource distributions, in accordance with one embodiment of the present invention;

FIG. 7 illustrates a user interface for calculating and the displaying the results of the retirement planning, in accordance with one embodiment of the present invention;

FIG. 8 illustrates a user interface for illustrating how the available resource amount is calculated, in accordance with one embodiment of the present invention;

FIG. 9 illustrates an optimization and goal process for optimizing the user's retirement planning, in accordance with one embodiment of the present invention; and FIG. 10 illustrates an optimization interface, in which the retirement planning interface is supplemented with additional potential selections for the user.

DETAILED DESCRIPTION OF THE INVENTION

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to elements throughout. Where possible, any terms expressed in the singular form herein are meant to also include the plural form and vice versa, unless explicitly stated otherwise. Also, as used herein, the term "a" and/or "an" shall mean "one or more," even though the phrase "one or more" is also used herein.

An "account" is the relationship that a user has with an entity, such as a financial institution. Examples of accounts include a deposit account, such as a transactional account (e.g., a banking account), a savings account, an investment account, a money market account, a time deposit, a demand deposit, a pre-paid account, a credit account, a non-monetary user profile that includes information associated with the user, or the like. The account is associated with and/or maintained by the entity. "Authentication information" is any information that can be used to identify of a user. For example, a system may prompt a user to enter authentication information such as a username, a password, a personal identification number (PIN), a passcode, biometric information (e.g., voice authentication, a fingerprint, and/or a retina scan), an answer to a security question, a unique intrinsic user activity, such as making a predefined motion with a user device. This authentication information may be used to authenticate the identity of the user (e.g., determine that the authentication information is associated with the account) and determine that the user has authority to access an account or system. An "entity" as used herein may be a financial institution. For the purposes of this invention, a "financial institution" may be defined as any organization, entity, or the like in the business of moving, investing, or lending money, dealing in financial instruments, or providing financial services. This may include commercial banks, thrifts, federal and state savings banks, savings and loan associations, credit unions, investment companies, insurance companies and the like. In some embodiments, the entity may allow a user to establish an account with the entity. To "monitor" is to watch, observe, or check something for a special purpose over a period of time. The "monitoring" may occur periodically over the period of time, or the monitoring may occur continuously over the period of time. In some embodiments, a system may actively monitor a database, wherein the system reaches out to the database and watches, observes, or checks the database for changes, updates, and the like. In other embodiments, a system may passively monitor a database, wherein the database provides information to the system and the system then watches, observes, or checks the provided information. "Retirement planning" in a financial context may refer to the allocation of resources and decisions made for the use of resources incoming and outgoing in an attempt to achieve financial independence, so that the need to be gainfully employed is optional rather than a necessity. "Retirement planning" may relate to anything that involves determining how the user should utilize resources in order to try to maximize the use of the asset to live. In some embodiments, retirement planning models estimate a user's income immediately prior to retirement and adjust this income downward to reflect an income necessary for the user to maintain a satisfactory lifestyle. In some embodiments, a retirement planning model incorporates the user's current health and medical history and extrapolate the annual living expenses through the years in retirement. In some embodiments, retirement planning may be provided to the user by a financial institution, or other entity. A "transaction" refers to any communication between a user and the financial institution or other entity monitoring the user's activities. For example, a transaction may refer to a purchase of goods or services, a return of goods or services, a payment transaction, a credit transaction, or other interaction involving a user's account. In the context of a financial institution, a transaction may refer to one or more of: a sale of goods and/or services, initiating an automated teller machine (ATM) or online banking session, an account balance inquiry, a rewards transfer, an account money transfer or withdrawal, opening a bank application on a user's computer or mobile device, a user accessing their e-wallet, or any other interaction involving the user and/or the user's device that is detectable by the financial institution. A transaction may include one or more of the following: renting, selling, and/or leasing goods and/or services (e.g., groceries, stamps, tickets, DVDs, vending machine items, and the like); making payments to creditors (e.g., paying monthly bills; paying federal, state, and/or local taxes; and the like); sending remittances; loading money onto stored value cards (SVCs) and/or prepaid cards; donating to charities; and/or the like.

Furthermore, a "user" may be a financial institution customer (e.g., an account holder or a person who have an account (e.g., banking account, credit account, or the like)). In one aspect, a user may be any financial institution customer involved in retirement planning with the financial institution or any other affiliate entities associated with the financial institution. In some embodiments, the user may be an individual who may be interested in opening an account with the financial institution. In some other embodiments, a user may be any individual who may be interested in enrolling in the retirement plan offered by the financial institution. In some embodiments, a "user" may be a financial institution employee (e.g., an underwriter, a project manager, an IT specialist, a manager, an administrator, an internal operations analyst, bank teller or the like) capable of operating the system described herein. For purposes of this invention, the term "user" and "customer" may be used interchangeably. A "user interface" is any device or software that allows a user to input information, such as commands or data, into a device, or that allows the device to output information to the user. For example, the user interface include a graphical user interface (GUI) or an interface to input computer-executable instructions that direct a processing device to carry out specific functions. The user interface typically employs certain input and output devices to input data received from a user second user or output data to a user. These input and output devices may include a display, mouse, keyboard, button, touchpad, touch screen, microphone, speaker, LED, light, joystick, switch, buzzer, bell, and/or other user input/output device for communicating with one or more users.

Usage of finite resources in a period of possible resource depletion can be difficult to navigate. Inefficient usage of resources can cause early depletion. Different geographic areas may provide differentiation in resource requirements, which can effect resource usage. By surveying the differences in geographic locations and determining optimized efficient resource usage, a system can provide an optimization resource usage plan.

Embodiments of the present invention address the above needs and/or achieve other advantages by providing apparatuses (e.g., a system, computer program product, and/or other device) and methods that improve resource usage planning, such as retirement planning, for users (e.g., customers) and allows the users to factor in different variables (e.g., age, spending amounts over time, events that may affect retirement planning, or the like).

Referring now to FIG. 1, the figure illustrates a geographic selection system environment 100, in accordance with some embodiments of the invention. The environment 100 includes a user device 111 associated or used with authorization of a user 9 (e.g., an account holder, a mobile application user, a bank customer, and the like), a third party system 160, and a financial institution system 140. In some embodiments, the third party system 160 corresponds to a third party financial institution. The environment 100 further includes one or more third party systems 192 (e.g., a partner, agent, or contractor associated with a financial institution), one or more other financial institution systems 194 (e.g., a credit bureau, third party banks, and so forth), and one or more external systems 196.

The systems and devices communicate with one another over the network 130 and perform one or more of the various steps and/or methods according to embodiments of the disclosure discussed herein. The network 130 may include a local area network (LAN), a wide area network (WAN), and/or a global area network (GAN). The network 13030 may provide for wireline, wireless, or a combination of wireline and wireless communication between devices in the network. In one embodiment, the network 130 includes the Internet.

The user device 111, the third party system 160, and the financial institution system 140 each includes a computer system, server, multiple computer systems and/or servers or the like. The financial institution system 140, in the embodiments shown has a communication device 142 communicably coupled with a processing device 144, which is also communicably coupled with a memory device 146. The processing device 144 is configured to control the communication device 142 such that the financial institution system 140 communicates across the network 130 with one or more other systems. The processing device 144 is also configured to access the memory device 146 in order to read the computer readable instructions 148, which in some embodiments includes one or more applications such as applications 150 and 151. The memory device 146 also includes a datastore 154 or database for storing pieces of data that can be accessed by the processing device 144.

As used herein, a "processing device," generally refers to a device or combination of devices having circuitry used for implementing the communication and/or logic functions of a particular system. For example, a processing device may include a digital signal processor device, a microprocessor device, and various analog-to-digital converters, digital-to-analog converters, and other support circuits and/or combinations of the foregoing. Control and signal processing functions of the system are allocated between these processing devices according to their respective capabilities. The processing device 114, 144, or 164 may further include functionality to operate one or more software programs based on computer-executable program code thereof, which may be stored in a memory. As the phrase is used herein, a processing device 114, 144, or 164 may be "configured to" perform a certain function in a variety of ways, including, for example, by having one or more general-purpose circuits perform the function by executing particular computer-executable program code embodied in computer-readable medium, and/or by having one or more application-specific circuits perform the function.

Furthermore, as used herein, a "memory device" generally refers to a device or combination of devices that store one or more forms of computer-readable media and/or computer-executable program code/instructions. Computer-readable media is defined in greater detail below. For example, in one embodiment, the memory device 146 includes any computer memory that provides an actual or virtual space to temporarily or permanently store data and/or commands provided to the processing device 144 when it carries out its functions described herein.

The user device 111 includes a communication device 112 communicably coupled with a processing device 114, which is also communicably coupled with a memory device 116. The processing device 114 is configured to control the communication device 112 such that the user device 111 communicates across the network 130 with one or more other systems. The processing device 114 is also configured to access the memory device 116 in order to read the computer readable instructions 118, which in some embodiments includes application 120 and online banking application 121. The memory device 116 also includes a datastore 122 or database for storing pieces of data that can be accessed by the processing device 114. The user device 111 may be a mobile device of the user 9, a bank teller device, a third party device, an automated teller machine, a video teller machine, or another device capable of capturing a check image.

The third party system 160 includes a communication device 162 communicably coupled with a processing device 164, which is also communicably coupled with a memory device 166. The processing device 164 is configured to control the communication device 162 such that the third party system 160 communicates across the network 130 with one or more other systems. The processing device 164 is also configured to access the memory device 166 in order to read the computer readable instructions 168, which in some embodiments includes an application 170. The memory device 166 also includes a datastore 172 or database for storing pieces of data that can be accessed by the processing device 164.

In some embodiments, the application 120, the online banking application 121, and the application 170 interact with the application 150 or 151 to receive or provide financial data, analyze financial record data, and implement business strategies, transactions, and processes. The applications 150 and 151 may be a suite of applications for performing these functions.

In some embodiments, the application 120, the online banking application 121, and the application 170 interact with the applications 150 and 151 to utilize metadata to determine decisions for processing.

The applications 120, 121, 150, 151, and 170 are for instructing the processing devices 114, 144 and 164 to perform various steps of the methods discussed herein, and/or other steps and/or similar steps. In various embodiments, one or more of the applications 120, 121, 150, 151, and 170 are included in the computer readable instructions stored in a memory device of one or more systems or devices other than the systems 160 and 140 and the user device 111. For example, in some embodiments, the application 120 is stored and configured for being accessed by a processing device of one or more third party systems 192 connected to the network 130. In various embodiments, the applications 120, 121, 150, 151, and 170 stored and executed by different systems/devices are different. In some embodiments, the applications 120, 121, 150, 151, and 170 stored and executed by different systems may be similar and may be configured to communicate with one another, and in some embodiments, the applications 120, 121, 150, 151, and 170 may be considered to be working together as a singular application despite being stored and executed on different systems.

In various embodiments, one of the systems discussed above, such as the financial institution system 140, is more than one system and the various components of the system are not collocated, and in various embodiments, there are multiple components performing the functions indicated herein as a single device. For example, in one embodiment, multiple processing devices perform the functions of the processing device 144 of the financial institution system 140 described herein. In various embodiments, the financial institution system 140 includes one or more of the external systems 196 and/or any other system or component used in conjunction with or to perform any of the method steps discussed herein. For example, the financial institution system 140 may include a financial institution system, a credit agency system, and the like.

In various embodiments, the financial institution system 140, the third party system 160, and the user device 111 and/or other systems may perform all or part of a one or more method steps discussed above and/or other method steps in association with the method steps discussed above. Furthermore, some or all the systems/devices discussed here, in association with other systems or without association with other systems, in association with steps being performed manually or without steps being performed manually, may perform one or more of the steps of one or more of the method discussed herein, or other methods, processes or steps discussed herein or not discussed herein.

FIG. 2 illustrates a retirement planning system environment 1, in accordance with an embodiment of the present invention. As illustrated in FIG. 2, the retirement planning systems 10 are operatively coupled, via a network 130 to the asset systems 20, the user computer systems 30, and other financial institution systems or third party systems (not illustrated). As discussed herein, in this way, the retirement planning systems 10 may be utilized by users 9 in order to plan for retirement using the features of the application described herein related to at least determining and recalculating an available resource amount that the user 9 has to spend over a period of time and an age parameter when the user's resources are reduced to a number that cannot cover estimated outflows, among the other features described herein. FIG. 2 illustrates only one example of embodiments of a retirement planning system environment 1, and it will be appreciated that in other embodiments one or more of the systems (e.g., computers, mobile devices, servers, or other like systems) may be combined into a single system or be made up of multiple systems.

As illustrated in FIG. 2, the retirement planning systems 10 generally comprise a communication device 12, a processing device 14, and a memory device 16. The processing device 14 is operatively coupled to the communication device 12 and the memory device 16. The processing device 14 uses the communication device 12 to communicate with the network 130 and other devices on the network 130, such as, but not limited to, the asset systems 20, the user computer systems 30, and other financial institution systems or third-party systems. As such, the communication device 12 generally comprises a modem, server, or other device for communicating with other devices on the network 130.

As further illustrated in FIG. 2, the retirement planning systems 10 comprise computer-readable instructions 18 stored in the memory device 16, which in one embodiment includes the computer-readable instructions 18 of a retirement planning application 17. In some embodiments, the memory device 16 includes a datastore 19 for storing data related to the retirement planning systems 10, including but not limited to data created and/or used by retirement planning application 17. As discussed above the retirement planning application 17 communicates over the network 130 to send and receive information from the asset applications 27, the web browser or applications 37 in the user computer systems 30, and/or other applications on other financial institution systems or third-party systems. For example, the retirement planning application accesses the values of the resources of users 9 over the network 130 from various servers, systems, and devices that store asset information of the users 9; determines estimated inflows and outflows from past inflows and outflows and any other significant future events over the network 130 from various servers, systems, and devices that store transaction information (e.g., accounts within the asset applications); calculates an available resource amount that a user 9 can spend over a period of time; calculates the an age parameter indicating the age at which the user's resources will not be able to cover the user's outflows; and displays the information in an interactive interface over the network 130 that allows the user 9 to make adjustments to the available resource amount and/or the age parameter.

As further illustrated in FIG. 2, the asset systems 20 generally comprise a communication device 22, a processing device 24, and a memory device 26. The processing device 24 is operatively coupled to the communication device 22 and the memory device 26. The processing device 24 uses the communication device 22 to communicate with the network 130, and other devices on the network 130, such as, but not limited to, the retirement planning systems 10, user computer systems 30, and other financial institution systems or third-party systems. As such, the communication device 22 generally comprises a modem, server, or other device(s) for communicating with other devices on the network 130.

As illustrated in FIG. 2, the asset systems 20 comprise computer-readable program instructions 28 stored in the memory device 26, which in one embodiment includes the computer-readable instructions 28 of an asset application 27. In some embodiments, the memory device 26 includes a datastore 29 for storing data related to the asset systems 20, including but not limited to data created and/or used by the asset application 27. The asset application 27 may be utilized by the retirement planning application 17 to access the resources of the user 9, such as through accessing the user's financial accounts (e.g., accounts that distribute resources with restrictions and accounts that can be converted to cash quickly), ownership of property and estimates of the value of the property, applications that track the transactions of the users 9 over time, or the like. This information or other like information accessed through the asset applications 27 is utilized by the retirement planning application 17 and displayed on the user computer systems 30 through a web browser/application 37.

As further illustrated in FIG. 2, the user computer systems 30 generally comprise a communication device 32, a processing device 34, and a memory device 36. The processing device 34 is operatively coupled to the communication device 32 and the memory device 36. The processing device 34 uses the communication device 32 to communicate with the network 130, and other devices on the network 130, such as, but not limited to, the retirement planning systems 10, the asset systems 20, and the other financial institution systems or the third-party systems.

As illustrated in FIG. 2, the user computer systems 30 comprise computer-readable program instructions 38 stored in the memory device 36, which in one embodiment includes the computer-readable instructions 38 of a web browser or application 37. In some embodiments, the memory device 36 includes a datastore 39 for storing data related to the user computer systems 30, including but not limited to data created and/or used by the a web browser or application 37. The a web browser or application 37 allows the user 9, in one embodiment, to communicate with the retirement application 17 and/or asset applications 27, as well as applications provided by the financial institution or other third-party, in order to access the retirement planning interface 400, send information to these applications, and receive information from these applications. In some embodiments a web browser is used to access websites, applications, or the like; however, in other embodiments a specific application (e.g., mobile application, computer application, or the like) is specifically configured to communicate with the other systems and applications within the retirement planning environment 1. In still other embodiments of the invention portions of other applications may be stored on the user computer systems 30, such as but not limited to the retirement planning application 27, the asset applications 37, or other applications.

The other financial institution systems or third-party system (both not illustrated) are operatively coupled to the retirement planning systems 10, asset systems 20, and user computer systems 30, through the network 130. The other financial institution systems and/or third-party systems have devices the same as or similar to the devices described for the retirement planning systems 10, asset systems 20, and user computer systems 30 (e.g., communication device, processing device, memory device with computer-readable instructions, datastore, or the like). Thus, the other financial institution systems and/or third-party systems communicate with the retirement planning systems 10, asset systems 20, user computer systems 30, and/or each other in the same or similar way as previously described with respect to the retirement planning systems 10, asset systems 20, and/or the user computer systems 30. The other financial institution systems and/or third-party systems, in some embodiments, provide additional information about the users 9, user's resources, or the like, which may be used by the retirement planning systems 10, or the like.

FIG. 3 illustrates a high level process flow for graphic selection based on resource allocation and distribution 800, in accordance with one embodiment of the present invention. As illustrated in block 802, the process 800 is initiated by generating a modeling tool. The modeling tool may be generated by the system and include a database and a real-time data extraction capability processing device. As such, the model may be able to extract and compute data from entity servers for calculation of geographic selection of resource allocation.

Next, as illustrated in block 804, the process 800 continues by identifying resource requirements for assistance, medical, and reconfigurations for the user. In some embodiments, resource requirements for assistance may include resource requirements for in home nursing, in home care, nursing home care, extended living care, or the like. In some embodiments resource requirements for medical may comprise an estimate of future requirements for medical expenses or the like associated with an aging individual. In some embodiments, resource requirements for reconfigurations, which include moving, downsizing, modifying an existing home, assisted living, or the like may incorporate a value of the current home of the user and any resource requirements for reconfiguration of living arrangements for the user.

As illustrated in block 806, the process 800 continues by comparing the requirements identified in block 804 to the user's resource availability. In this way, the system, via the model, may review resource availability of a user through one or more financial institutions associated with the user.

Once the comparison has been generated, the model generates a specific model for the user that is associated with the comparison, as illustrated in block 808. The generated model may be presented to the user via a display on the user device and illustrate a modeling of various potential outcomes if the user continues to live in his/her current location and required remodeling, medical, and aging expenses. Alternatively, the model presents a potential outcome if the user decides to relocate to a different home, assisted living, or the like and the required expenses associated therewith. Finally, the model will illustrate those options in comparison with the user's current resource availability to present a location most appropriate based on resource allocation, health, and requirements of the user.

Finally, as illustrated in block 810, the system may present the model in a form of an alternative decision tool to a trusted individual associated with the user. The trusted individual may be a family member, friend, insurance company, doctor, nurse, or the like illustrating the options and one or more selections of the same.

Furthermore, the model may be integrated with a mechanism for the sharing of information to trusted individuals throughout the process of modeling such that the decision processing may be taking place during the process and not specifically presenting the final modeling to the user and trusted individual at the final stage.

FIG. 4 illustrates a high-level process flow for retirement planning based on resource distributions 101, in accordance with some embodiments of the invention. As illustrated by block 102 of FIG. 4, embodiments of the invention comprise determining a user's resources and the values of the resources (e.g., balances of the account, current or estimated future fair market values of the property, or the like). The user's resources may include but are not limited to checking accounts, savings accounts, investment accounts (e.g., with regular dispersements and penalties for principal withdrawals, or self-directed accounts that more liquid without penalties), annuity accounts (e.g., social security, claim awards, reverse mortgages, or the like), insurances benefit accounts (e.g., one time or reoccurring), property owned by the user (e.g., investment property, rental property, or the like), or other like resources that may provide regular or semi-regular recurring payments, resources that are or are similar to cash accounts, or resources that need to be sold in order to realize cash values of the resources. In some embodiments the resources may be illiquid (e.g., have penalties or may take time to convert into cash) or may be liquid (e.g., can be converted to cash in a couple of days without penalty). In some embodiments all of the resources are determined in order to get an idea of what the values of the resources are in order to determine how long the inflows and outflows for the user may last.

As illustrated by block 103 in FIG. 4, embodiments of the invention further include determining past inflows of resources received from or deposited into the user's resources (e.g., user's accounts, or the like), such as paychecks, 401K disbursements, pension disbursements, or the like. Block 103 further illustrates that past outflows of resources from the user's resources (e.g., user's accounts, or the like) are determined, such as payments for housing (e.g., rent or mortgage), bills, health care insurance and other costs, heat, water, food, or like, which illustrates all of the essential (e.g., necessary or necessary to the user) costs that cover what the user currently uses to live.

Block 104 of FIG. 4 illustrates that the financial institution determines estimated future inflows and outflows over one or more time periods (e.g., daily, weekly, bi-weekly, monthly, yearly, averages of each, for multiple specific time periods in the future, or the like). The estimated inflows and outflows are based on the user's past inflows and outflows, future scheduled inflows and outflows, the inflows and outflows that the financial may determine will exist in the future, and/or other like estimates. The estimates made for the inflows and outflows by the financial institutions may account for seasonal changes, one time large expenses, knowledge of a change in the user's life, such as moving to a different house, no longer supporting a dependent child, parent, friend, or the like, or any other inflow or outflow that may occur for the user 9.

As illustrated by block 105 in FIG. 4 the estimated available resource amount that the user can spend per period of time may be calculated based on the estimated inflows and outflows from the users resources, such as the user's accounts that provide a distribution of resources to the user and the user's account with which the user pays for expenses. The estimated available resource amount that the user can spend illustrates the amount of money a user can spend above the user's cost of living expenses for entertainment, vacations, gifts, or other like non-essential expenses (e.g., fun money, safe to spend amount, or the like) while maintaining enough resources to reach a certain age (e.g., age parameter at which the user's resources will be depleted and will no longer be able to cover the outflows).

As illustrated by block 106 in FIG. 4, either after, at the same time, or before the estimated available resource amount is calculated an estimated age parameter is calculated that illustrates based on the user's resources, estimated inflows, and estimated outflows the age at which the user will run out of resources, or stated another way when the user's outflows are greater than the user's inflows and the user has no additional resources to cover the difference. For example, at the same time the resources from the user's resources are flowing into the user's cash accounts, or other like accounts, the values (e.g., balances) where the resource inflows are coming from are being depleted (e.g., with the exception of annuity type resources such as social security benefits, life annuity payments, pension inflows, or the like). There comes a point in time in which the value of the user's resources (e.g., accounts, resources that the user has mortgaged, or the like) are depleted and the user can no longer cover the outflows.

Block 107 of FIG. 4 illustrates that the user 9 may be allowed to change the available resource amount per the time period (e.g., week, bi-weekly, monthly, six month, yearly, or the like) and/or the age parameter, for example in order to recalculate the available resource amount and/or recalculate the age parameter to identify how long the resources will last based on how much the user 9 wants to spend per the time period, or to identify how much the user 9 can spend based on how long the user 9 wants the resources to last. This information can be controlled and displayed in user interfaces described in further detail later.

It should be understood that when describing a user throughout this invention, the use of the term user may be replaced by users, which indicates that the invention may also include pulling information from the accounts of one or more users (e.g., customers). The multiple users may include a household of people (e.g., husband and wife, parent and child, multiple family members, or the like), which may determine the available resources amount and/or the age parameter for multiple users, for example a household. In still other embodiments, with respect to the actions that a user may take that are described herein, the user may allow or designate another family member, a financial advisor, an estate planner, a trustee, or the like (e.g., otherwise described as a designee) in order to take an action in place of the user. These designees may use the information available to the user for retirement planning purposes during retirement of the user and/or after the user passes away to help plan the user's retirement and/or distribute the user's resources.

FIG. 5 illustrates a flow chart indicating how the available resource amount and/or an age parameter are influenced 209, in accordance with one embodiment of the invention. Block 210 illustrates a number of resources, such as types of accounts, investments, annuities, property, or the like that may provide a stream of income (or negative steam of income) or payments over a period of time, but which may also be illiquid or otherwise difficult to convert into cash. For example, types of resources that provide disbursements may be a 401K that requires minimum disbursements to the user 9 over a period of time at a specific age; an IRA that requires minimum disbursements to the user 9 over a period of time at a specific age; a pension account that may provide disbursements until the user 9 passes away; insurance benefits that may be distributed as an annuity for a period of time or as a lump sum; a trust account from which disbursement are made, property that provides rental income to the user 9, social security income or death benefits that pays disbursements for a period of time (e.g., a specific amount of time or for the life of a beneficiary), or other like annuity. In some embodiments of the invention the resources may include estimated rates of returns such that not only are the disbursements used in determining the available resource amount and/or age parameter, but the principal and growth of the principal over time may be used in determining the available resource amount and/or age parameter.

Block 220 illustrates that the user 9 may also have a full-time and/or part time job that provides additional income inflows, such as supplemental employment income inflows, to the user 9 and/or user accounts. The amount of estimated supplemental employment income may be determined based on the hours that the user 9 works, which may be estimated over a period of time, and as such be increased, diminished, or stop based on the age of the user, the number of hours worked over time, increases or decreases in pay over time, and/or other factors that may indicate how long a user 9 may have supplemental income in the future.

As illustrated by block 210 and 220 the inflows from disbursement accounts or other resources, and/or the inflows from supplemental employment income inflow, may be utilized directly to pay for outflows, and thus, be used to calculate the available resource amount illustrated in block 250 described below. In other embodiments of the invention the inflows from disbursement accounts or other resources, and/or the inflows from supplemental employment income inflow may be distributed to liquid or semi-liquid accounts, described in further detail below with respect to block 230.

Block 230 illustrates liquid (e.g., liquid or semi-liquid) resources, such as accounts that may be equivalent to cash or resources that can be converted quickly into cash. For example, the liquid accounts may be checking accounts, savings accounts, self-directed investment accounts, money market accounts, or the like. These liquid accounts may be utilized to pay for the outflows directly as illustrated by block 240 in Figure B_US1_2, which are discussed in further detail later. In some embodiments these types of accounts may be one of the last accounts that may be utilized to pay for outflows after the inflows from block 210 are exhausted (e.g., with the exception of lifetime annuity accounts). Some of these accounts may also have rates of return (e.g., savings accounts, self-directed investment accounts, or the like) which may be factored in when calculating the available resource amount and/or the age parameter.

As illustrated in block 240 the outflows of the users 9 may include the payments that the user 9 makes in order to live (e.g., necessary or semi-necessary to the user for the living expenses of the user 9). For example, in some embodiments the outflows may include housing outflows, which may cover the expenses of the user 9 for mortgage payments, taxes, insurance, or the like that the user 9 has to pay in order to maintain a residence. In other examples, the outflows may be related to bills, such as electric, gas, water, or the like.

The user's health care cost, such as user's health care premiums and yearly estimated cost may be included. The user 9 may have car payments that are due on a monthly (or other time period) basis. The user 9 may also have insurance payments for the user's car, life, or the like. In addition, there may be other outflows, such as but not limited to child care payments, cell phone payments, internet, and/or other entertainment expenses that may or may not be included in the outflow calculations (e.g., may or not be considered essentials or semi-essentials). The outflows may also include some life event outflows that may be easily predictable, non-repeating outflows, and/or only periodic outflows (e.g., occurs more than the time period for which the outflows are calculated), such as but not limited to paying for a child's college, paying for a wedding, or other like life events that affect the user's outflows. As illustrated by block 210, 220, and 230 some of these outflows may be paid by one or more of the inflows, the supplemental employment income inflow, and/or the liquid resources either directly or indirectly. As such, one or more of the user's resources may have a balance that is depleted over time as the outflows are paid.

Block 250 illustrates the available resource amount per the time period is determined by taking the difference between the inflows and outflows. As such, the available resource amount illustrates the amount of money that a user 9 has to spend above the user's outflows per the time period. For example, the available resource amount may be utilized by the user 9 to spend on trips, electronics, entertainment (e.g., dinners, moves, shows, or the like), to spend on family members, or the like. The available resource amount is the amount of money that the user 9 is safe to spend over the time period, without spending negative amounts of money on the outflows.

As illustrated by block 260, the available resource amount may be utilized, along with the user's resources in order to determine an age parameter at which the user's resources are estimated to be depleted. As such, the age parameter illustrates the age at which the user 9 will not be able to cover the outflows. For example, as the user's inflows from block 210 are depleted, there becomes a point in time when the user's inflows will not cover the user's outflows. At this point in time, the outflows will be covered by the balances of the user's liquid resources (e.g., cash accounts or other like cash accounts). As such, a calculation for an age parameter may be made when the total resources of the user (e.g., inflows from resources and liquid asset accounts) would not cover the outflows for the user. In some embodiments the age parameter may be infinity as the user's inflows are so great (e.g., payments received in dividends, interest rates, rental payments received) that they will never be depleted enough to be less than the user's outflows.

Block 270 illustrates that in some embodiments the user 9 may not spend the available resource amount, and as such depending on the how the outflows were paid, the unspent resource amount may be reinvested into the liquid resources (e.g., self-directed accounts, checking accounts, savings accounts, or the like) or back into more illiquid resources, such as purchases of property or other non-liquid resources.

It should be understood that the determination of the available resource amounts over the time period and/or the age parameter may change in real-time or near real-time as the rate of return on the resources change (e.g., stock values change, rental income changes or goes away, resources are depleted, big purchases are made or sold, or the like), and costs change (e.g., damage to property than needs repair, variable interest rate changes, life events occur that deplete resources, loans are taken out or paid off, or the like). As such, the present invention may be constantly in real-time or near real time, or over various intervals, recalculated in order to provide a more accurate available resource amount and/or age parameter to the user 9, such that the user 9 is better able to plan for retirement. Moreover, as illustrated in further detail later the user 9 may be able to adjust the available resource amount and/or the age parameter in order to determine how changes in spending habits affect the age at which the user's resources are depleted, or vice versa.

FIG. 6, illustrates a detailed process flow for retirement planning based on resource distributions 301, in accordance with some embodiments of the invention. As illustrated by block 302, the financial institution receives an indication that a customer (e.g., a type of user 9) wants to evaluate the customer's resources for retirement. For example, the customer may access a retirement planning interface (e.g., described in further detail later) and requests that the financial institution evaluates the customer's retirement resources.

As illustrated by block 304, the financial institution may access user information for the user, such as not but not limited to the user's age, lifestyle, geographic location, health history (e.g., through medical expenses, food purchases, or information disclosed by the user 9), and thereafter determine the same and/or average peer information for similar users of the same age, health history, or the like and use the average statistics to determine the life expectancy of the user's peers, the estimated inflows and estimated outflows of the user's peers, and/or the average resources, and rates of return on each, of the user's peers. This information may be utilized, in part, in order to estimate the future inflows, outflows, resources, rates of return, or the like.

Block 306 illustrates that the financial institution accesses the resources of the customer (e.g., the resources described with respect to blocks 210 and 230 in FIG. 5). For example, the financial institution accesses asset information from the customer's accounts that the financial institution services. The customer may also allow the financial institution to access the customer's accounts with other third-parties and/or financial institutions. Moreover, the financial institution may evaluate other resources that the financial institution knows that the customer owns, such as for example the financial institution has information about the property that the customer's own, and thus can evaluate the value of the asset and/or the future value over of the asset over time.

It should be understood that with respect to blocks 306 and 308, as well as otherwise described herein, in some embodiments of the invention the current and/or future fair market value of the resources may be determined by accessing third-party servers, systems, devices, applications, or the like in order to determine the fair market values. For example, the financial institution may access websites that provide estimates of home values, car values, antique values, or the like.

Block 310 illustrates that the financial institution determines the past/future resource inflows for the customer. For example, the financial institution can determine the amount of resources that the customer has received from various accounts within and outside of the financial institution over time. With respect to the accounts serviced by the financial institution the financial institution has access to the past/future resource inflows. With respect to accounts located outside the financial institution the past resource inflows may be determined by identifying the inflow of resources into the accounts held by the financial institution. Moreover, as previously discussed the customer may allow the financial institution to access the customer's accounts to determine any past/future resources that the customer may receive from various resources. Moreover, the financial institution may determine the resources of the customer that have yet to provide inflows (e.g., 401k accounts that cannot be accessed until a specific age, or the like). In some embodiments the financial institution may estimate the future inflow of resources, for example, if the customer receives the same payments continuously in consecutive time periods the financial institution may continue to estimate the same resource receipts in future time periods.

In some embodiments, the customer (e.g., user 9) may have resources that only the customer is aware of, and as such the customer may provide an indication of the unidentified resources to the financial institution to include in the financial institution's calculation of the user's resources and/or resource in-flows. In some embodiments the unidentified resources may include money being paid back for a loan provided by the customer that the financial institution does know about, the customer is a beneficiary of an account that the financial institution does not know about, the customer is a silent partner in business that the financial institution does not know about, or the like.

In some embodiments, the financial institution may analyze the outflows in order to determine what may qualify as an outflow that is necessary (e.g., necessary or semi-necessary to cover cost of living expenses), such as mortgages, heat, water, gas, phone, internet, or the like, from any discretionary spending that may cover payments the user 9 may make for entertainment (e.g., trips, dinner out, movies, shows, presents, or the like), such as payments that would be covered by the calculated available resource amount. As such, the transactions made by the user 9 that may be discretionary may be utilized to determine an estimated available resource amount that the user 9 is currently spending, which may be augmented by inflation rates in order to determine what the available resource amount may be in the future. As such, the available resource amount may be set in order to determine what the user likely wants to have available to the user 9 in the future, and which may be utilized to determine the age parameter.

Block 312 illustrates that the financial institution determines the estimated future inflows that the customer receives based on the past inflows and future inflows determined from block 310. The financial institution may determine the estimated inflows that the customer may receive (e.g., may decide to receive, may be required to receive based on applicable laws, or the like) in the future. The estimated inflows may be averaged over a one or more time periods (e.g., short term, long term, or the like), may be determined for one or more time periods, or may be determined until reaching the age parameter.

Block 314 illustrates that the financial institution determines the past/future resource outflows for the customer. For example, the financial institution can determine the amount of resources that customer has paid from various accounts within and outside of the financial institution over time. With respect to the accounts serviced by the financial institution the financial institution has access to the past/future resource outflows by examining the payments that the customer has made over time (e.g., in the past) and/or has scheduled in the future. In some embodiments the financial institution may estimate the future outflow of resources, for example, if the customer makes the same payments continuously in consecutive time periods the financial institution may continue to estimate the same payment in future time periods. For example, the financial institution can determine the amount of resources that the customer has sent for payment from various accounts within and outside of the financial institution over time. With respect to accounts located outside the financial institution the past resource outflows may be determined by identifying the outflow of resources from the accounts held by the customer at outside financial institution that are received by the financial institution. Moreover, as previously discussed the customer may allow the financial institution to access the customer's accounts at the outside financial institutions to determine any past/future resources that the customer may have sent from various resources. In some embodiments the financial institution may estimate the future outflow of resources, for example, if the customer makes the same payments continuously in consecutive time periods the financial institution may continue to estimate the same payments in future time periods.

Block 316 illustrates that the financial institution determines the estimated future outflows that the customer pays based on the past outflows and future outflows determined from block 314. The financial institution may determine the estimated outflows that the customer may pay (e.g., may decide to pay, may be required to pay based on applicable laws, payments made, or the like) in the future. The estimated outflows may be averaged over a one or more time periods (e.g., short term, long term, or the like), may be determined for one or more time periods, or may be determine until reaching the age parameter.

The financial institution may calculate an available resource amount based on the estimated future inflows and outflows, as illustrated by block 318. For example, the financial institution may determine the current available resource amount based on the current inflows and outflows for the current time period, the estimated future available resource amount based on the estimated future inflows and outflows for any time period in the future, or an average available resource amount based on the average inflows and outflows for multiple time periods. As discussed, in some embodiments the available resource amount may be an average available resource amount over multiple periods of time, a specific estimated available resource amount for a specific future time period, and specific average available resource amount for a specific future time periods, an estimated range of the available resource amount for one or more time periods, or any other current or future available resource amount for any time period or time period range (e.g., seasonal, yearly, monthly, or the like).

As illustrated by block 320 the financial institution calculates an age parameter that is based on the estimated inflows, estimated outflows, and the customer's resources. For example, the financial institution (e.g., through the retirement planning systems 10 and/or the retirement planning application 17) uses the customer's current age, calculates how the inflows will deplete the user's resources over time, calculates how the outflows will be paid using the user's resources (e.g., illiquid resources and/or liquid resources), calculates when the outflows exceed the inflows and the user's liquid resources or illiquid resources have to be sold to cover the outflows, and when the resources from all of the user's resources are depleted such that the customer cannot cover the outflows, and finally the financial institution calculates the point in time when the user's resources are depleted and determines the age of the customer at this point in time. In some embodiments, the financial institution not only calculates the age parameter when the resources of the customer are depleted, but also calculates the time at which the customer's liquid resources may have to be sold. For example, if the user owns rental property and the customer's inflows have been depleted to a point in which the inflows and/or liquid resources no longer would cover the outflow, the financial institution may determine that age at which the user needs to sell the property in order to cover the outflows. In other embodiments, this may apply to other illiquid resources, such as but not limited to cars, boats, annuity payments that can be sold for a lump sum, or the like.

Moreover, in other embodiments of the invention if the customer has lifetime annuities, and/or inflows, the financial institution may also determine the point at which a customer must reduce the user's outflows in order to allow the customer's inflows to cover the customer's outflows. For example, the financial institution may determine the age parameter at which the customer's inflows and resources will no longer cover the customer's outflows. At this lifestyle change age parameter the customer may still have inflows from lifetime benefits (e.g., lifetime annuities, lifetime pensions, or the like), but such inflows may not cover the customer's outflows. As such, the customer may continue to live off of the inflows, but the customer may have to change his/her outflows. For example, the customer may be required to sells the customer's home and move to a less expensive home or rental property, in addition the customer may also have to reduce other types of expenses as well. In this way, the financial institution may also determine a new reduced available resource amount on which the customer can now live on based on lifetime annuities and the customers reduced outflow expenses. In some embodiments the new age parameter may also be extended based on the reduced outflows, or even extended indefinitely because of the lifetime inflows.

As illustrated in block 322 the financial institution (e.g., through the retirement planning systems and/or the retirement planning application 17) may display the information discussed in blocks 302 to 320 in one or more interfaces, such as a retirement planning interface 400 and/or an available resource amount interface 500. The interfaces, as discussed in further detail later, may include the current and/or estimated outflows and/or inflows, the current and/or future estimated available resource amounts, and/or the estimated age parameter, and any depleted available resource amount and/or depleted age parameter calculated from lifetime inflows, as well as any averages for one or more time periods for any of these calculations.

In addition, as discussed in further detail later, block 324 illustrates that the financial institution also displays in the one or more interfaces potential life events that the customer may select to improve the estimated available resource amount and/or the age parameter. For example, life events that are certain to occur, or have a chance of occurring, may change the resources and/or the inflows or outflows of the customer, and may be utilized to adjust the available resource amount and/or the age parameter in order to provide more accurate retirement planning. In addition to the life events, the present invention may also allow the user to input specific behaviors that the user takes in order to see how the behaviors affect the user's age parameter or available resources amount. The behaviors may be daily, weekly, monthly or other like behaviors (e.g., transactions, purchases, savings strategies, investment strategies, or the like), which the user 9 may currently make or the user may want to make in the future. By selecting the behaviors the user 9 can determine how cutting out the behavior or adding the behavior may change the available resource amount and/or the age parameter.

Block 326 illustrates the financial institution (e.g., through the retirement planning systems 10, the retirement planning application 17, and/or the interfaces 400, 500 discussed in further detail later) receives an indication from the customer to adjust the available resource amount. As illustrated by block 328, and discussed in further detail later with respect to the interfaces 400, 500 the financial institution (e.g., through the retirement planning systems 10 and/or the retirement planning application 17) recalculates a new age parameter and displays it in the interfaces 400, 500.

Block 330 illustrates that the financial institution (e.g., through the retirement planning systems 10, the retirement planning application 17, and/or the interfaces 400 discussed in further detail later) receives an indication from the customer to adjust the age parameter. As illustrated by block 332, and discussed in further detail later with respect to the interfaces 400, 500 the financial institution (e.g., through the retirement planning systems 10 and/or the retirement planning application 17) recalculates a new available resource amount and displays it in the interfaces 400, 500.

In some embodiments of the invention the life event may include a medical expense, a child moving back home or leaving home, the death of a spouse, inheritance, unexpected income, a trip to plan, or other like major life event that may occur. The user 9 may select one of the life events, and the financial institution may provide cost estimates for the life events automatically based on the experience of the financial institution systems that track similar life events for other users. Alternatively, the user 9 may add specific costs associated with the life event in order to determine how the life event will affect the available resources amount and/or the age parameter.

In some embodiments of the invention the behaviors may include transactions that the user 9 is thinking about adding or removing from the user's outflows or from using the available resources on. For example, the user 9 may select a behavior in order to determine the cost savings if the user 9 decides to cut out the transaction. For example, the user 9 may cut out a five (5) dollar cup of a coffee that the user purchases 5 days a week. The user 9 may input the cost information, and in response the financial institution may determine how the cost of the transaction (e.g., coffee) would increase based on inflation in the future and determine how much money the user would save if the user cut out the transaction (e.g., coffee) altogether, or replaced it with a less expensive alternative behavior (e.g., cost of tea, water, making coffee at home, or the like). The financial institution may determine the alternative behavior and the cost of the alternative behavior through transactions of other users that the financial institution has access to. The age parameter and the available resources amount are recalculated to illustrate how the change in the behavior affects the retirement planning. In another example, the user 9 may decide that he is going to start buying movie channels through the user's cable package. The financial institution may estimate the additional cost outflow of the change and provide an indication how the additional costs over time would affect the user's available resource amount and/or the user's age parameter.

The financial institution may store information related to the costs of specific behaviors based on transaction information from the financial institution's customers (e.g., the financial institution knows the average cost of the behavior, or the cost of the behavior for a peer of the user). In other embodiments, the financial institution may be able to access this type cost information from third-parties (e.g., the third-parties know the average cost of the behavior, or the cost of the behavior for a peer of the user). In still other embodiments of the invention, the user 9 may provide the cost information related to the behavior (e.g., the user may input the cost into the retirement planning interface). The financial institution may determine how the costs might change over time based on inflation information, changes in the frequency of the behavior (e.g., as the person ages the person may perform the behavior more or less), estimated changes of the cost of the behavior vs. other behaviors over time (e.g., cost of the behavior decreases vs. inflation), or the like.

Block 334 illustrates that the financial institution (e.g., through the retirement planning systems 10, the retirement planning application 17, and/or the interfaces 400 discussed in further detail later) receives an indication from the customer to add a life event to adjust the retirement planning. As illustrated by block 336, and discussed in further detail later with respect to the interfaces 400, 500 the financial institution (e.g., through the retirement planning systems 10 and/or the retirement planning application 17) recalculates a new available resource amount and a new age parameter and displays it in the interfaces 400, 500.

FIG. 7 illustrates a retirement interface 400, which in one embodiment illustrates user information 402 (e.g., customer information) related to the name of the user, profile picture, or the like. The retirement interface 400 may also comprises a plan summary section 410, which may illustrate a plan status section 412 and a plan resource summary 414. The plan status section 412 may include an indication if the user is currently ahead of the desired retirement plan, on pace with the desired retirement plan, or behind the desired retirement plan (e.g., user retirement plan goals). For example, in some embodiments the user 9 may select a particular desired available resource amount that the user 9 would like to spend over a period of time (e.g., monthly) the user may also select a desired age parameter for which the user 9 would like the user's resources to last. After the financial institution determines the user's estimated available resource amount and estimated age parameter the financial institution (e.g., the retirement planning systems 10 and/or the retirement planning application 17), through the retirement planning interface 400, may display and indication whether or not the desired available resource amount and/or the desired age parameter meets the estimated available resource amount and/or the estimated age parameter in the plan status section 412. The plan resource summary section 414 may illustrate the user's current or estimated future resource inflows, resource outflows, and the available resource amount (e.g., safe to spend amount) that the use may spend on top of meeting the user's expenses. For example, the available resource amount in the plan resource summary section 414 may display what the user's current available resource amount is for the current time period (e.g., the current month). In other embodiments, the plan resource summary section 414 may illustrate an available resource amount for a future time period. For example, since these numbers may change over time because the user's inflows, outflows, and rates of return on the resources will change over time, the user 9 may select a future time period for which the user would like to see a summary in the plan resource summary section 414. The selection of the future time period may occur through a calendar selection, a drop down list section, search selection, or the like. Regardless of the selection, the plan summary section 414 may illustrate estimates of the future inflows, future outflows, and the available resource amount for one or more future time periods selected by the user. In other embodiments the financial institution may select the one or more future time periods to display to the user 9. For example, the financial institution may decide elect to illustrate the seasonal changes in the future inflows, future outflows, and the available resource amount (e.g., changes between the fall, winter, spring, and summer); may elect to illustrate yearly changes in the future inflows, future outflows, and the available resource amount (e.g., averages for each year in the future and estimated changes in the averages, or estimates at the beginning, middle, and/or end for each year); may elect to illustrate whenever there is a change in the future inflows, future outflows, and the available resource amount (e.g., only display the estimates when the estimates change, such as one estimate for the first six months, estimates for the next two months when they change, or the like); or any other patterns in displaying the future inflows, future outflows, and the available resource amount.

The retirement planning interface 400 may also illustrate a financial planning estimator section 420, which may include an available resource amount estimator section 422 and an age parameter estimator section 424. The available resource amount and age parameter initially provided in the available resource amount estimator section 422 and the age parameter estimator section 424 may be the initial values determined by the financial institution, as previously described herein. The available resource amount estimator section 422 may allow a user 9 to identify the impact on the user's retirement plan by changing the available resource amount per a time period (e.g., the user may select a per month selection feature 426), or identifying the impact of a one-time expense (e.g., the user may select a one-time expense selection feature 428). With respect to the changing the available resource amount per a time period the user may utilize an available resource amount selector (e.g., the slide feature illustrated in FIG. 4, a blank input, drop-down menu, or any other like selector) to change the estimated available resource amount to illustrate how changing the spending amount affects the calculation of the age parameter illustrated in the age parameter estimator section 424. For example, decreasing the available resource amount the user 9 spends may increase the age parameter, while increasing the available resource amount the user 9 spend may decrease the age parameter. The change may be linear or non-linear in that small changes vs. large changes in the available resource amount may result in expediential changes in the age parameter due to the time value of money, the return on investment rate over time, the age of the user, the value of the resources, or the like.

In other embodiments of the invention, the user 9 may change the age parameter (e.g., decrease or increase the age parameter by 1, 5, 10, or like years) in the age parameter estimator section 424 and the available resource estimator section 422 changes the available resource amount that the user may have to spend over a time period (e.g., on average for a range of time periods, a particular time period, and/or multiple time periods). In some embodiments when the user 9 changes the available resource amount and/or the age parameter the plan summary section 410 may also update based on the new estimates, and display different estimates over one or more time periods based on the changes made by the user 9 to the available resource amount and/or the age parameter.

The same changes may be illustrated in the retirement planning interface 400 if the user estimates a one-time expense. For example, if the user selects the one-time selection feature 428, a one-time expense section may be presented to the user 9 (not illustrated). The user 9 may enter the value of the one-time expense in the one-time expense section. For example, the user 9 may be purchasing a car, house, boat, furniture, or another type of one-time expense. The user 9 may input in estimated one-time expense, and as such the financial institution (e.g., the retirement planning system and/or the retirement planning application 17) may factor in the reduction of the user's resources (e.g., reduction in the amount in a cash account, reduction in the amount of a retirement asset, and/or lease to pay for the one-time purchase, or the like) and calculate new estimated available resource amount and/or estimated age parameter. The retirement planning summary section 410 may also be updated based on the one-time expense. As such, the user 9 may be able to factor in how a potential one-time expense will affect the user's retirement plan.

The retirement planning interface 400 also has a life event section 440, which illustrates some life events that may affect the user's future retirement plan. Some life events may include a potential medical expense, a child or parent that the user 9 is tasked with supporting, a death of a spouse or dependent, an inheritance, unexpected income, a trip, a move to another area, or other like life event. In some embodiments, the user 9 may select one or more of these life events, in order to factor in one or more of the life events into the user's retirement plan. The financial institution (e.g., through the retirement planning systems 10 and/or the retirement planning application 17) may access external services and/or internal databases in order to determine how much such a life event may cost. For example, in some embodiments the user 9 might select a medical expense and specify a particular type of medical issue, such as a knee replacement. Continuing with the example, the financial institution (e.g., through the retirement planning systems 10 and/or the retirement planning application 17) may access medical institutions, insurance institutions, and/or medical payments in order to determine how much a knee replacement typically costs. In some embodiments, the user 9 and/or the financial institution may factor in how much would be paid by insurance and how much would come out of the user's resources. Furthermore, the financial institution (e.g., through the retirement planning systems 10 and/or the retirement planning application 17) may access the user's resources to determine from which accounts the medical expenses should be paid. With respect to having to support a child or parent the financial institution may access internal or external services that have applications which indicate the estimated costs for supporting a child moving back in with his parents or support a dependent parent based on the dependent parent's age and medical condition. In still other embodiments, with respect to the death of a spouse the financial institution my adjust the resources, inflows, and outflows in order to determine new estimated available resource amounts and age parameters. In other embodiments the financial institution (e.g., through the retirement planning systems 10 and/or the retirement planning application 17) may factor in an inheritance that the user 9 may receive in the future (e.g., actual inheritance, or an estimated inheritance), may factor in unexpected income from a part time job, lotto winnings, or the like. In other embodiments the financial institution (e.g., through the retirement planning systems 10 and/or the retirement planning application 17) may factor in expenses, such as a trip, payment to a dependent, setting up a trust account, or the like which may all affect the user's financial planning. As such the financial institution (e.g., through the retirement planning systems 10 and/or the retirement planning application 17) may recalculate the inflows, outflows, the available resource amount, and/or the age parameter based on the life events.

In some embodiments of the invention a custom life event that is not specifically presented to the user 9 by the financial institution in the retirement planning interface 400 may be added by the user 9, which may include adding the type of life event, as well as the associated costs of the life event and the costs that may be attributable to user 9. The financial institutions (e.g., through the retirement planning systems 10 and/or the retirement planning application 17) may recalculate the inflows, outflows, the available resource amount, and/or the age parameter based on the life event added by the user.

In some embodiments of the invention, in addition to selecting a life event or adding a custom life event the user 9 may indicate the likelihood of the occurrence of the life event, such as percentage which the financial institution (e.g., through the retirement planning systems 10 and/or the retirement planning application 17) may use to discount the benefit or cost of the associated with the life event. For example, the user 9 may estimate that a medical expense is only 50% likely to occur, and as such the financial institution may reduce the affect that the medical expense has on the inflows, outflows, the available resource amount, and/or the age parameter when compared to if the medical expense was 100% certainty. This likelihood of occurrence factor may be applied to any life event selected or custom life event added by the user 9.

FIG. 8 illustrates another embodiment of the invention, in which additional information is presented to the user 9 regarding how the available resource amount is being determined. In some embodiments, an available resource amount interface 500 may be presented to the user 9, for example in a pop-window as illustrated in FIG. 8, or in other embodiments another type of interface. The available resource amount interface 500 may include information regarding how the user's available resource amount is determined. In one embodiment, as illustrated in FIG. 8 the available resource amount interface 500 may illustrate an inflow section 510 (e.g., inflow list, graph, table, or the like) that illustrates from where the inflows are being received and the amount of each of the inflows for a time period selected by the user or presented by the financial institution. The available resource amount interface 500 may also include an outflow section 520 (e.g., outflow list, graph, table, or the like) that illustrates from where the outflows are being received and the amount of each of the outflows for the time period selected by the user or presented by the financial institution. In still other embodiments inflow links 512 and outflow links 522 in the interface may be selected by the user 9 in order to take the user 9 to an activity list illustrating all of the user's inflow and outflow for a particular time period.

FIG. 9 illustrates an optimization and goal process 600 for optimizing the user's retirement planning and/or for achieving the retirement goals of the user 9. As illustrated by block 602 the financial institution receives an indication from a user to optimize the retirement planning of the user 9, such as an indication received from user through the retirement planning interface 400 previously described. For example, in one embodiment of the invention the user 9 may not like the calculation that the financial institution made with respect to the available resource amount and/or the age parameter, and as such, the user 9 may want to receive information related how to optimize (e.g., improve, increase, or the like) the available resource amount and/or the age parameter.

In one embodiment, as illustrated by block 604 the user 9 may request to optimize the available resource amount and/or the age parameter through one type of optimization parameter, which may comprises determining another location to which the user 9 may move to extend the time for which the user's resources may last (e.g., and optimized location parameter). In one embodiment of the invention, as illustrated in block 604 the financial institution may access the user's accounts to determine locations in which the user 9 has made transactions in order to determine one or more locations (e.g., one or more geographic regions, states, counties, cities, towns, developments, or the like) that the user 9 has visited, and as such, may have family, friends, may like to visit, or the like. In one embodiment, the financial institution may identify where the user's cars are registered to determine a new location. In other embodiments, the financial institution may identify the beneficiaries of the user 9 and where the beneficiaries live (e.g. through transaction information, listed addresses, or the like). In still other embodiments, the financial institution may determine where the user 9 pays state income tax in order to determine a new location for the user 9. In other embodiments of the invention, the financial institution may identify one or more locations that the financial institution may suggest, or may have suggested in the past, which may have lower cost of living expenses than the user's current location. In still another embodiment, the user 9 may select a new location to which the user 9 is interested in moving, and the financial institution may provide information related to the changes in the available resource amount and age parameter based on the requested location selected by the user 9. The financial institution may have access to, or may access third-party websites in order to determine, the cost of living in the locations (e.g., current user location and one or more potential new locations). The financial institution may compare the cost of living of the current user location with the cost of loving of the one or more potential new locations, and identify one or more new locations to which the user 9 could relocate to reduce the user's outflows. The financial institution may recalculate the available resource amount and age parameter using the cost of living expenses (e.g., housing, food, heating, cooling, television, phone, property taxes, gas, or the like) for the one or more new locations, in order to determine a location specific optimized available resource amount and an a location specific optimized age parameter. The financial institution may display the location specific optimized available resource amounts and location specific optimized age parameters for the one or more new locations verses the user's available resource amount and age parameter for the user's current location in the retirement planning interface 400.

While the above contemplates relocation to a different geographic area, as illustrated in block 605, in some instances, a customer may be more interested not in a change of geographic location but in a change of living arrangements. For example, a customer may be contemplating whether to remain in their home or move into a senior living, assisted living, and healthcare facility. While assisted living and healthcare facilities may, at first blush, seem expensive, the cost of maintenance, upkeep, and retrofitting of the customer's home may outweigh the cost of moving into an assisted living or healthcare facility. The system may provide a modeling tool for pre-retirees and retirees for determination of location of living when aging. The modeling tool may take into consideration costs for assisted living, medical expenses, user's budget and expenses, remodeling of current home requirements, and the like. The model may determine or provide options and prices for aging in place or in a care facility. The system may compare costs to living in home, including modifications to the home required for living in place, home health care, and the like compared to costs of care facilities in the area. The model is generated based on finances and health, such as illnesses, or the like that may impact the living selection. The system may provide a decision tool to trusted family members, doctors for input on determination, and insurance providers.

In this variation, with reference to block 604 the user 9 may request to optimize the available resource amount and/or the age parameter through one type of optimization parameter, which may comprise determining the difference between remaining in their home versus moving to a care facility. In one embodiment of the invention, as illustrated in block 604 the financial institution may access the user's accounts to determine various information regarding the user's home, home location, home maintenance records, and the like. The system may also seek input form the user regarding the condition of the home, any upgrades to the home that is in place or needed to assist the user as they age. For example, the system may request information regarding the convenience of the home, such as if it is a one-story or a two-story home. It may request information regarding railings, stairs, bathroom configuration, or the like The system may also access external databases regarding location of the home and convenience to services, such as doctor's facilities, pharmacy, senior centers, shopping centers, public transportation, or the like that might affect a user's ability to live in the home.

The system may use financial records, health records, and/or user input to determine the user's state of health, any limitations on living alone or with assistance, any particular health issues that require specific assistance, or the like The system may also predict future health issues associated with user, either based on the user's current health, projection issues, or the like These predicted health issues may have timing projections, cost projections, or the like The system may access real estate records to determine home pricing for similarly situated homes. The system may also assess the value of the user's home and the amount of money, if any, owed on the home to determine the equity in the home. The system may also access external data associated with home maintenance schedules (i.e., lifespans of various home features, such as windows, air conditioning systems, plumbing, and the like), repairs, cost of retrofitting homes for senior care, and the like to access not only the current value of the home, but costs associated with maintaining and upgrading of the home.

The system may also access external information associated with home healthcare costs and the costs for transportation to health facilities and other health related appointments as a contrast to these costs if the user was in a care facility.

The system may also determine various other home living expenses, such as utility bills, food, and other living essentials that would be otherwise provided in a care facility. In short, the system may determine/project large categories of expenses that the user may incur with remaining in their home as they age. These costs can provide in the aggregate, or they can be provided on a year by year basis. In the year by year basis display, the system may show how costs may increase overtime, dues to projected healthcare cost increases, added projected health issue of the user, and other factors.

The system may also access external information to determine cost for care facilities in either the local area or in a geographic location either predicted or selected by the user. The system will determine differences between the various costs between living in the user's home and moving to a care facility, such as housing costs, living expenses, healthcare expenses, transportation, or the like. Finally, the system will provide output to the user highlighting differences in cost between the two options of living in one's house versus relocating to a care facility. The system may also provide predictive models based on predicted home prices, economic data, user healthcare needs, or the like that may assist the user in determining when to transition from home living to a care facility based on economic value.

In another embodiment of the invention, as illustrated by block 607, the system may use user information, such as financial information, health information, user input, and the like to compare against various programs, such as governments subsidies, insurance subsidies, grants, charity programs, company incentives, coupons, rebates, sales, loans, and the like, that user may be eligible for based on their particular situation. The system includes a database listing the various available programs. Incorporating a rules engine or other logic, the system compares the user's data to each program and determines potential matches, such as for example, income level, location of program, age, status, or the like of the user. These potential matches may be displayed to the user for action. In some embodiments, the system may include forms needed for the user to apply to a matching program. The may prepopulate the form with user information and highlight to the user needed information. The system may also electronically submit, track, update, and provide alerts regarding the user's application to the program. In some instances, where the user and the program are a "near" match, the system may provide the user with various guidelines and steps that the user may take to qualify for the program.

In another embodiment of the invention, as illustrated by block 606, the user 9 may request to optimize the available resource amount and/or the age parameter through one type of optimization parameter, which may be based on investment decisions, inflow decisions, and/or outflow decisions of peers of the user 9 (e.g., peer optimization). As previously discussed, peers may include people that have similar peer information as the user information of the user 9. For example, the user information and peer information may include but is not limited to the age, lifestyle (e.g., based on transactions), geographic location, health history, investment risk, transactions, interests, products (e.g., goods and services) purchased, or the like of the user and the user's peers. For example, the financial institution may have access to the peer information because the peers are also customers of the financial institution, or may pull general information from third-parties. As such, the financial institution may identify one or more peers (e.g., specific or anonymous people, or specific or anonymous groups of people) of the user 9 and analyze the resource-inflows and resource-outflows of the peers, and/or the available resource amount and/or age parameter of the peers compared to the same information of the user 9. In other embodiments of the invention the financial institution may compare goals of the user 9 with the goals of peers (e.g., explained in further detail later). The financial institution may identify peer decisions, for example investment decisions, investment risk, purchases, geographic locations for living, types of housing, inflows, outflows, or other transactions, or the like associated with the peers. The financial institution determines how the user 9 may adjust the user's decisions with respect to the user's resources, inflows, outflows, or the like to improve upon the available resource amount, the age parameter, and/or the retirement planning of the user 9 based on the user's decisions. For example, if the user's peers are invested in resources with a guaranteed return of 4% and are less risky, while the user is invested in resources that may result in estimated returns of negative 8% to positive 8%, the financial institution may suggest different investments for the user 9. As an example, the financial institution may suggest to the user to investing less risky resources. Moreover, the financial institution may determine that the user's peers spend less on housing and food than the user 9. As such, the financial institution may provide suggestions to the user to reduce the user's housings and food costs. In other example, the financial institution may also identify the resources the user's peers use to pay for expenses during different year, and as such may suggest to the user 9 specific accounts and amounts from the accounts that the user 9 should use to cover the user's transactions. Moreover, in addition to the suggest tips, the financial institution may provide an updated available resource amount and/or age parameter based on the suggested user decisions determined from the decisions of the user's peers. In other embodiments of the invention, the financial institution may provide other types of suggestions for the user based on the actions of the user's peers.

In another embodiment of the invention, as illustrated by block 608, the user 9 may request to optimize the available resource amount and/or the age parameter through one type of optimization parameter, which may be based on products (e.g., services, or the like) that the financial institution or another third-party (e.g., other financial institution) may provide to the user 9 to increase the user's resources and/or resource-inflows and decrease the user's resource-outflows (e.g., financial product optimization). The financial institution may extend, or find another third-party to extend, available loans, re-financing, asset distribution (e.g., taking distributions based on reducing tax savings), asset to cash conversion (e.g., selling property, converting stocks that are declining into cash, or the like), cash to investment conversion (e.g., purchase bonds, mutual resources, high yield dividend stocks, or the like with idle cash), or the like. The financial institution may evaluate the user's resources in order to determine products that the financial institution (or other third-party) may offer the user 9. For example, the financial institution may identify that the user's mortgage rate is high and the user 9 may be able to save resources by refinancing. In other embodiments, the financial institution may be able to provide a mortgage to the user at a low interest rate (e.g., 3.5%) and invest the resources for the user 9 in a stock that has a 5% dividend. In still other embodiments of the invention, the financial institution may indicate to the user 9 that the user should convert the user's idle cash to bonds in order to receive interest on the bonds. The suggestions provided by the financial institution may be made by the financial institution to the user 9 through the retirement planning interface on the user device. Moreover, when presenting a suggested product to the user 9 the financial institution may also recalculate the available resource amount and/or the age parameter and display these along with the suggested products being offered.

As illustrated by block 610, after determining different optimization parameters (e.g., either requested by the user or suggested by the financial institution) the financial institution may display the suggested asset, inflow and/or outflow optimization parameters, and the updated estimated optimized available resource amount and optimized age parameter to the user through the retirement planning interface 400. The optimization of the user's retirement plan is designed to increase the available resource amount and/or the age parameter for the user 9.

Block 612 of FIG. 9 illustrates that in some embodiments of the invention the user 9 may set savings and/or retirement goals, which the user 9 would like to meet. In one embodiment, the goals may include an age to which the user 9 would like his/her resources to last or an available resource amount for one or more time periods. For example, if the available resource amount and/or the age parameter, or the optimized versions of each, are not enough to meet the user's goals, than the user 9 may indicate a desired available resource amount goal and/or a desired age parameter goal. In response to the goals the financial institution may present tips or suggestions on how the user 9 may reach the desired goals. For example, the financial institution may provide the optimization information described with respect to blocks 604 through 608 described above, or other like tips or suggestions. As discussed with respect to block 610 the tips or suggestions may be presented to the user 9 in the user interface (e.g., retirement planning interface 400).

As illustrated by block 614, the financial institution may monitor the user' transactions over time and compare the transactions (e.g., resource-inflows and resource-outflows) to the user's retirement planning (e.g., available resource amount and/or age parameter). For example, the financial institution may identify that the user's inflows are the same as previously estimated, but the user's outflows are less than what was previously estimated. However, the financial institution may also identify that the user 9 is 50% over the available resource amount calculated for the user 9 in one or more time periods (e.g., in one month, in two consecutive months, two out of three months, or the like). In some embodiments, the financial institution may provide an alert to the user, or an advisor (e.g., parent, child, guardian, financial advisor or the like) of the user, indicating that the user 9 is spending outside of the user's retirement plan related to the available resource amount. However, the alert may also include an indication that the user's inflows have remained on plan, and the user's outflows are less than what was estimated. As such, the reduction in the outflows may cover a portion of the overspending relating to the available resource amount, and this information may all be included in the alert to the user 9 and/or the user's guardian. In this way, the user 9 and/or the user's advisor may become aware of if the user is on plan, over plan, or underplan and take the necessary steps to make any reductions in costs or increases to spending or additional reinvestment. The alert may be any type of one or more alerts, such as but not limited to an e-mail, pop-up notification in the interface, message sent through the retirement planning interface or another interface, text message, phone call, mail letter, or the like. The alert may include a recalculation of the user's available resource amount and/or age parameter to illustrate how a new available resource amount that is based on the increased spending (or in other embodiments decreased spending) of the user 9 per a time period will negatively (or positively) affect the age parameter. For example, if the user has spent on average 50% more than the available resource amount for three straight months, the alert may include an estimate of the new available resource amount (e.g., increased estimate) and how the increased spending, if continued, would reduce the age parameter at which the user's resources would be depleted.

FIG. 10 illustrates an optimization interface 700, in which the retirement planning interface 400 previously described above is supplemented with additional potential selections for the user 9. For example, in one embodiment the optimization interface 700 includes an optimization section 710 and a retirement goal section 800. The optimization section 710, may include one or more optimization selections, which may or may not have been previously described herein. In one embodiment the optimization selections may include a geographic optimization section 712, a peer based optimization section 714, a financial action optimization section 716, and/or another optimization section 718. The user 9 may select any one of these optimization selections in order for the financial institution to access the information described above with respect to FIG. 9, or other information, in order to optimize the user's resources for retirement planning for increasing the user's available resource amount and/or increasing the user's age parameter. In some embodiments an optimization interface may be provided that allows the user 9 to receive additional information from the financial institution regarding optimization based on the user's selection (e.g., additional geographic information, peer information, financial action, and/or the like, as discussed above). The financial institution may present the optimized available resource amount in the optimization section and/or it may be displayed in the same sections described with respect to the retirement planning interface 400.

The optimization interface 700, or other interface described herein, in some embodiments, may also include a retirement goal section 800 (e.g., or a separate goal interface). As described above with respect to FIG. 9, the user may select and/or input a desired available resource amount goal that is a goal of the user's to reach. In other embodiments, this selection may alternatively occur in the planning estimator section 420 described with respect to the retirement planning interface 400. This may set a particular goal in which the user 9 would like to reach. Alternatively, or in addition to selecting a desired available resource amount, the user 9 may also select and/or input a set desired age parameter goal for which the user 9 is interesting in reaching with the user's resources. In response, the financial institution may provide tips or suggestions to the user 9 that may allow the user 9 to reach the user's goals. For example, the financial institution may display the tips or suggestions in the suggestions section 830 of the interface. In one embodiment, the tips or suggestions may include the amount of additional inflows that the user 9 must bring in based on a supplemental income, improved rates on the user's investments, reduced outflow amounts, reduced discretionary spending, or the like, as previously discussed.

As will be appreciated by one of ordinary skill in the art, the present invention may be embodied as an apparatus (including, for example, a system, a machine, a device, a computer program product, and/or the like), as a method (including, for example, a business process, a computer-implemented process, and/or the like), or as any combination of the foregoing. Accordingly, embodiments of the present invention may take the form of an entirely software embodiment (including firmware, resident software, micro-code, and the like), an entirely hardware embodiment, or an embodiment combining software and hardware aspects that may generally be referred to herein as a "system." Furthermore, embodiments of the present invention may take the form of a computer program product that includes a computer-readable storage medium having computer-executable program code portions stored therein. As used herein, a processor may be "configured to" perform a certain function in a variety of ways, including, for example, by having one or more special-purpose circuits perform the functions by executing one or more computer-executable program code portions embodied in a computer-readable medium, and/or having one or more application-specific circuits perform the function. As such, once the software and/or hardware of the claimed invention is implemented the computer device and application-specific circuits associated therewith are deemed specialized computer devices capable of improving technology associated with the in authorization and instant integration of a new credit card to digital wallets.

It will be understood that any suitable computer-readable medium may be utilized. The computer-readable medium may include, but is not limited to, a non-transitory computer-readable medium, such as a tangible electronic, magnetic, optical, infrared, electromagnetic, and/or semiconductor system, apparatus, and/or device. For example, in some embodiments, the non-transitory computer-readable medium includes a tangible medium such as a portable computer diskette, a hard disk, a random access memory (RAM), a read-only memory (ROM), an erasable programmable read-only memory (EPROM or Flash memory), a compact disc read-only memory (CD-ROM), and/or some other tangible optical and/or magnetic storage device. In other embodiments of the present invention, however, the computer-readable medium may be transitory, such as a propagation signal including computer-executable program code portions embodied therein.

It will also be understood that one or more computer-executable program code portions for carrying out the specialized operations of the present invention may be required on the specialized computer include object-oriented, scripted, and/or unscripted programming languages, such as, for example, Java, Perl, Smalltalk, C++, SAS, SQL, Python, Objective C, and/or the like. In some embodiments, the one or more computer-executable program code portions for carrying out operations of embodiments of the present invention are written in conventional procedural programming languages, such as the "C" programming languages and/or similar programming languages. The computer program code may alternatively or additionally be written in one or more multi-paradigm programming languages, such as, for example, F #.

It will further be understood that some embodiments of the present invention are described herein with reference to flowchart illustrations and/or block diagrams of systems, methods, and/or computer program products. It will be understood that each block included in the flowchart illustrations and/or block diagrams, and combinations of blocks included in the flowchart illustrations and/or block diagrams, may be implemented by one or more computer-executable program code portions. These one or more computer-executable program code portions may be provided to a processor of a special purpose computer for the authorization and instant integration of credit cards to a digital wallet, and/or some other programmable data processing apparatus in order to produce a particular machine, such that the one or more computer-executable program code portions, which execute via the processor of the computer and/or other programmable data processing apparatus, create mechanisms for implementing the steps and/or functions represented by the flowchart(s) and/or block diagram block(s).

It will also be understood that the one or more computer-executable program code portions may be stored in a transitory or non-transitory computer-readable medium (e.g., a memory, and the like) that can direct a computer and/or other programmable data processing apparatus to function in a particular manner, such that the computer-executable program code portions stored in the computer-readable medium produce an article of manufacture, including instruction mechanisms which implement the steps and/or functions specified in the flowchart(s) and/or block diagram block(s).

The one or more computer-executable program code portions may also be loaded onto a computer and/or other programmable data processing apparatus to cause a series of operational steps to be performed on the computer and/or other programmable apparatus. In some embodiments, this produces a computer-implemented process such that the one or more computer-executable program code portions which execute on the computer and/or other programmable apparatus provide operational steps to implement the steps specified in the flowchart(s) and/or the functions specified in the block diagram block(s). Alternatively, computer-implemented steps may be combined with operator and/or human-implemented steps in order to carry out an embodiment of the present invention.

While certain exemplary embodiments have been described and shown in the accompanying drawings, it is to be understood that such embodiments are merely illustrative of, and not restrictive on, the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

INCORPORATION BY REFERENCE

To supplement the present disclosure, this application further incorporates entirely by reference the following commonly assigned patent applications:

| U.S. Patent Application Ser. No. | Title | Filed On |
|---|---|---|
| 15/223,469 | SYSTEM FOR TRIGGERING OF LIVING OPTION RESOURCE ALLOCATION | Jul. 29, 2016 |
| 15/223,667 | SYSTEM FOR A GEOGRAPHIC LOCATION BASED SHARING REQUEST NETWORK | Jul. 29, 2016 |
| 15/223,558 | WEARABLE DEVICE FOR REAL-TIME MONITORING OF PARAMETERS AND TRIGGERING ACTIONS | Jul. 29, 2016 |
| 15/223,880 | SYSTEM ENVIRONMENT FOR USER-SPECFIC PROGRAM AGGREGATION AND NON-COLLOCATED THIRD PARTY SYSTEM EXTRACTION AND DEPLOYMENT | Jul. 29, 2016 |

What is claimed is:

1. A system for accessing and analyzing resources for retirement planning, the system comprising:
one or more memory devices; and
one or more processing devices operatively coupled to the one or more memory devices, wherein the one or more processing devices are configured to execute computer-readable program code to:
access the resources of a user over a network of servers, wherein the resources include illiquid resources and liquid resources;
determine asset values;
determine user information, wherein user information comprises medical and age information for the user;
determine resource in-flows and resource out-flows for the resources over a past time period by requesting access to one or more financial accounts of the user and extracting transaction history for the resources;
calculate estimated future resource in-flows and estimated future resource out-flows over a future time period from at least the resource in-flows and the resource out-flows;
calculate estimated rates of return for the resources that provide returns by requesting access to one or more financial accounts associated with the user and extracting financial transaction information;
determine selected location preferences for the user, where selected location preferences are geographic locations for user relocation based on identification of user account activity at the geographic locations and geographic location preferences from the user;
generate a model of the selected location preferences of the user and alternative locations identified for the user;
maintain the model of the selected location preferences of the user and the alternative locations in real-time;
calculate location selection options for the user within the user's estimate future resource in-flows and estimated future resource out-flows, based on the selected location preferences and the alternative locations identified compared to the estimated future resource in-flows and estimated future resource out-flows over the future time period from at least the resource in-flows and the resource out-flows, wherein calculating location selection options further comprises identifying a resource amount required for the location for one or more time periods and an age parameter;
access an external database containing additional information for the location selection options and determine service locations associated with the location selection options, wherein determining the service locations comprises determining a convenience to access the service locations from the location selection options;
receive input regarding the user's current living situation, wherein the current living situation comprises the user's current home location, home maintenance records, and home accessibility features;
compare the user's current living situation with the location selection options and determining a subset of location selection options, wherein the subset of location selection options provides an increase in asset values, or an increase in home accessibility features;
compare the additional information for each of the subset of location selection options, wherein the comparison provides a determination of each of the subset of location selection option's service locations;
display the subset of location selection options to the user using the model via a display on a device associated with the user, wherein displaying the subset of location selection options to the user using the model via a display on a device associated with the user further comprises an interactive map overlay of the subset of location selection options for user selection overlaying a current display screen; and
generate, upon display of the location selection options to the user, a decision tool that is queued and sent to one or more trusted individual associated with the user and illustrates the location selection options and the user selected location selection options for implementation, wherein the trusted individual is a family member and resource allocation planner.

2. The system of claim 1, wherein receiving location selection preferences from a user further comprises providing the user with an interactive display that includes location selection preferences such as staying in a current location, remodeling the current location, moving to an alternative location, or moving to a care facility.

3. The system of claim 1, wherein an available resource amount indicates estimated resources the user is safe to spend on the location based on the user's estimate future resource in-flows and estimated future resource out-flows, wherein the age parameter indicates an estimated age when asset values will be depleted, and wherein the available resource amount for the time period and the age parameter are based at least in part on the asset values, the estimated rates of return, the estimated future resource in-flows and the estimated future resource out-flows.

4. The system of claim 1, wherein the model considers real-time resource requirements for assisted living, medical expenses, remodeling of current location, and user in-flows and out-flows.

5. The system of claim 1, wherein the location preferences or alternative locations comprise a current home, modification of the current home, care facilities, home health care, or alternative living arrangements.

6. A computer program product for accessing and analyzing resources for retirement planning, the computer program product comprising at least one non-transitory computer-readable medium having computer-readable program code portions embodied therein, the computer-readable program code portions comprising:

an executable portion configured for accessing the resources of a user over a network of servers, wherein the resources include illiquid resources and liquid resources;

an executable portion configured for determining asset values;

an executable portion configured for determining user information, wherein user information comprises medical and age information for the user;

an executable portion configured for determining resource in-flows and resource out-flows for the resources over a past time period by analyzing requesting access to one or more financial accounts of the user and extracting transaction history for the resources;

an executable portion configured for calculating estimated future resource in-flows and estimated future resource out-flows over a future time period from at least the resource in-flows and the resource out-flows;

an executable portion configured for determining calculating estimated rates of return for the resources that provide returns by requesting access to one or more financial accounts associated with the user and extracting financial transaction information;

an executable portion configured for determining selected location preferences for the user, where selected location preferences are geographic locations for user relocation based on identification of user account activity at the geographic locations and geographic location preferences from the user;

an executable portion configured for generating a model of the selected location preferences of the user and alternative locations identified for the user;

an executable portion configured for maintaining the model of the selected location preferences of the user and the alternative locations in real-time;

an executable portion configured for calculating location selection options for the user within the user's estimate future resource in-flows and estimated future resource out-flows, based on the selected location preferences and the alternative locations identified compared to the estimated future resource in-flows and estimated future resource out-flows over the future time period from at least the resource in-flows and the resource out-flows, wherein calculating location selection options further comprises identifying a resource amount required for the location for one or more time periods and an age parameter;

an executable portion configured for accessing an external database containing additional information for the location selection options and determining service locations associated with the location selection options, wherein determining the service locations comprises determining a convenience to access the service locations from the location selection options;

an executable portion configured for receiving input regarding the user's current living situation, wherein the current living situation comprises the user's current home location, home maintenance records, and home accessibility features;

an executable portion configured for comparing the user's current living situation with the location selection options and determining a subset of location selection options, wherein the subset of location selection options provides an increase in asset values, or an increase in home accessibility features;

an executable portion configured for comparing the additional information for each of the subset of location selection options, wherein the comparison provides a determination of each of subset of location selection option's service locations;

an executable portion configured for displaying the subset of location selection options to the user using the model via a display on a device associated with the user, wherein displaying the subset of location selection options to the user using the model via a display on a device associated with the user further comprises an interactive map overlay of the subset of location selection options for user selection overlaying a current display screen; and an executable portion configured for generating, upon display of the location selection options to the user, a decision tool that is queued and sent to one or more trusted individual associated with the user and illustrates the location selection options and the user selected location selection options for implementation, wherein the trusted individual is a family member and resource allocation planner.

7. The computer program product of claim 6, wherein receiving location selection preferences from a user further comprises providing the user with an interactive display that includes location selection preferences such as staying in a current location, remodeling the current location, moving to an alternative location, or moving to a care facility.

8. The computer program product of claim 6, wherein an available resource amount indicates estimated resources the user is safe to spend on the location based on the user's estimate future resource in-flows and estimated future resource out-flows, wherein the age parameter indicates an estimated age when asset values will be depleted, and wherein the available resource amount for the time period and the age parameter are based at least in part on the asset values, the estimated rates of return, the estimated future resource in-flows and the estimated future resource out-flows.

9. The computer program product of claim 6, wherein the model considers real-time resource requirements for assisted living, medical expenses, remodeling of current location, and user in-flows and out-flows.

10. The computer program product of claim 6, wherein the location preferences or alternative locations comprise a current home, modification of the current home, care facilities, home health care, or alternative living arrangements.

11. A computer-implemented method for accessing and analyzing resources for retirement planning, the method comprising:
   providing a computing system comprising a computer processing device and a non-transitory computer readable medium, where the computer readable medium comprises configured computer program instruction code, such that when said instruction code is operated by said computer processing device, said computer processing device performs the following operations:
   accessing the resources of a user over a network of servers, wherein the resources include illiquid resources and liquid resources;
   determining asset values;
   determining user information, wherein user information comprises medical and age information for the user;
   determine resource in-flows and resource out-flows for the resources over a past time period by analyzing requesting access to one or more financial accounts of the user and extracting transaction history for the resources;
   calculating estimated future resource in-flows and estimated future resource out-flows over a future time period from at least the resource in-flows and the resource out-flows;
   determine calculate estimated rates of return for the resources that provide returns by requesting access to one or more financial accounts associated with the user and extracting financial transaction information;
   determining selected location preferences for the user, where selected location preferences are geographic locations for user relocation based on identification of user account activity at the geographic locations and geographic location preferences from the user;
   generating a model of the selected location preferences of the user and alternative locations identified for the user;
   maintaining the model of the selected location preferences of the user and the alternative locations in real-time;
   calculating location selection options for the user within the user's estimate future resource in-flows and estimated future resource out-flows, based on the selected location preferences and the alternative locations identified compared to the estimated future resource in-flows and estimated future resource out-flows over the future time period from at least the resource in-flows and the resource out-flows, wherein calculating location selection options further comprises identifying a resource amount required for the location for one or more time periods and an age parameter;
   accessing an external database containing additional information for the location selection options and determining service locations associated with the location selection options, wherein determining the service locations comprises determining a convenience to access the service locations from the location selection options;
   receiving input regarding the user's current living situation, wherein the current living situation comprises the user's current home location, home maintenance records, and home accessibility features;
   comparing the user's current living situation with the location selection options and determining a subset of location selection options, wherein the subset of location selection options provides an increase in asset values, or an increase in home accessibility features;
   comparing the additional information for each of the subset of location selection options, wherein the comparison provides a determination of each of subset of location selection option's service locations;
   displaying the subset of location selection options to the user using the model via a display on a device associated with the user, wherein displaying the subset of location selection options to the user using the model via a display on a device associated with the user further comprises an interactive map overlay of the subset of location selection options for user selection overlaying a current display screen; and
   generating, upon display of the location selection options to the user, a decision tool that is queued and sent to one or more trusted individual associated with the user and illustrates the location selection options and the user selected location selection options for implementation, wherein the trusted individual is a family member and resource allocation planner.

12. The computer-implemented method of claim 11, wherein receiving location selection preferences from a user further comprises providing the user with an interactive display that includes location selection preferences such as staying in a current location, remodeling the current location, moving to an alternative location, or moving to a care facility.

13. The computer-implemented method of claim 11, wherein an available resource amount indicates estimated resources the user is safe to spend on the location based on the user's estimate future resource in-flows and estimated future resource out-flows, wherein the age parameter indicates an estimated age when asset values will be depleted, and wherein the available resource amount for the time period and the age parameter are based at least in part on the asset values, the estimated rates of return, the estimated future resource in-flows and the estimated future resource out-flows.

14. The computer-implemented method of claim 11, wherein the model considers real-time resource requirements for assisted living, medical expenses, remodeling of current location, and user in-flows and out-flows.

* * * * *